United States Patent
Py et al.

(10) Patent No.: US 9,725,228 B2
(45) Date of Patent: *Aug. 8, 2017

(54) FLUID DISPENSER HAVING A ONE-WAY VALVE, PUMP, VARIABLE-VOLUME STORAGE CHAMBER, AND A NEEDLE PENETRABLE AND LASER RESEALABLE PORTION

(75) Inventors: Daniel Py, Larchmont, NY (US); Joseph M. Ting, Fairfield, CT (US)

(73) Assignee: DR. PY INSTITUTE LLC, New Milford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/572,145

(22) Filed: Aug. 10, 2012

(65) Prior Publication Data

US 2013/0175299 A1 Jul. 11, 2013

Related U.S. Application Data

(63) Continuation of application No. 11/351,716, filed on Feb. 10, 2006, now Pat. No. 8,240,521, which is a
(Continued)

(51) Int. Cl.
*B65D 37/00* (2006.01)
*B65D 83/00* (2006.01)
(Continued)

(52) U.S. Cl.
CPC ........ *B65D 83/0055* (2013.01); *A61F 9/0008* (2013.01); *B05B 11/0043* (2013.01);
(Continued)

(58) Field of Classification Search
CPC . B65D 83/0055; B65D 81/245; A61F 9/0008; B05B 11/0043; B05B 11/0072;
(Continued)

(56) References Cited

U.S. PATENT DOCUMENTS 1,392,600 A 10/1921 Rose
1,471,091 A 10/1923 Bessesen
(Continued)

FOREIGN PATENT DOCUMENTS

CA 1123792 5/1982
CN 2436454 6/2001
(Continued)

OTHER PUBLICATIONS

International Search Report and Written Opinion for International Application No. PCT/US/2013/36296 issued Aug. 30, 2013. 12 pages.

(Continued)

*Primary Examiner* — Patrick M Buechner
(74) *Attorney, Agent, or Firm* — McCarter & English, LLP

(57) ABSTRACT

A dispenser for dispensing a fluid includes a rigid vial that has a main fluid chamber containing a fluid, and a pump assembly that is in fluid communication with the main fluid chamber and is configured to dispense a predetermined quantity of fluid from the main fluid chamber. A flexible bladder is provided which is located within the main fluid chamber and is configured to expand to fill the ullage created within the main fluid chamber during dispensing of fluid by the pump assembly. The resilient bladder tends to force itself outwardly toward the rigid vial and, in turn, increases the pressure within the main fluid chamber in comparison to the interior of the bladder to thereby prevent the ingress of air or vapors through the bladder or otherwise into the main fluid chamber.

18 Claims, 20 Drawing Sheets

Related U.S. Application Data continuation of application No. 10/890,465, filed on Jul. 12, 2004, now Pat. No. 7,000,806, which is a continuation of application No. 10/001,745, filed on Oct. 23, 2001, now Pat. No. 6,761,286.

(60) Provisional application No. 60/242,595, filed on Oct. 23, 2000, provisional application No. 60/242,974, filed on Oct. 24, 2000.

(51) Int. Cl.
  *A61F 9/00* (2006.01)
  *B05B 11/00* (2006.01)
  *B65D 81/24* (2006.01)

(52) U.S. Cl.
  CPC ...... *B05B 11/0072* (2013.01); *B05B 11/0097* (2013.01); *B05B 11/3004* (2013.01); *B05B 11/3074* (2013.01); *B05B 11/3077* (2013.01); *B05B 11/3092* (2013.01); *B05B 11/3094* (2013.01); *B65D 81/245* (2013.01)

(58) Field of Classification Search
  CPC .............. B05B 11/0097; B05B 11/3004; B05B 11/3074; B05B 11/3077; B05B 11/3092; B05B 11/3094; B65B 3/003
  USPC ......... 222/95, 105, 183, 206, 207, 209, 212, 222/320, 321.1, 321.2, 321.6, 386.5, 222/402.1–402.25, 491–494
  See application file for complete search history.

(56) References Cited

U.S. PATENT DOCUMENTS

| | | | |
|---|---|---|---|
| 1,641,534 A | | 9/1927 | Davis |
| 1,854,458 A | * | 4/1932 | De Quincy et al. .......... 222/215 |
| 2,014,881 A | | 9/1935 | Carlstrom |
| 2,246,693 A | | 6/1941 | Ohme |
| 2,317,270 A | | 4/1943 | Harris |
| 2,471,852 A | | 5/1949 | Bau |
| 2,503,147 A | | 4/1950 | Applezweig |
| 2,649,995 A | | 8/1953 | Muskin |
| 2,667,986 A | | 2/1954 | Perelson |
| 2,715,980 A | | 8/1955 | Frick |
| 2,740,556 A | | 4/1956 | Baron |
| 2,751,119 A | | 6/1956 | Manning, Sr. |
| 2,844,285 A | | 7/1958 | Moran |
| RE24,918 E | * | 1/1961 | Mills .......................... 222/386.5 |
| 3,055,367 A | | 9/1962 | Thorstad |
| 3,092,278 A | | 6/1963 | Järnhäll |
| 3,136,440 A | | 6/1964 | Krug et al. |
| 3,160,329 A | | 12/1964 | Radic et al. |
| 3,166,096 A | | 1/1965 | Lang |
| 3,173,579 A | | 3/1965 | Curie et al. |
| 3,180,374 A | | 4/1965 | Muller |
| 3,193,128 A | | 7/1965 | Ravn |
| 3,211,340 A | | 10/1965 | Zander |
| 3,220,611 A | | 11/1965 | Zander |
| 3,231,149 A | | 1/1966 | Yuza |
| 3,278,063 A | | 10/1966 | Kranzhoff |
| 3,340,671 A | | 9/1967 | Loo |
| 3,343,422 A | | 9/1967 | McSmith |
| 3,392,859 A | | 7/1968 | Fischer |
| 3,416,425 A | * | 12/1968 | Rigolini ...................... 396/392 |
| 3,424,329 A | | 1/1969 | Hersherg et al. |
| 3,499,582 A | | 3/1970 | Berney |
| 3,507,568 A | | 4/1970 | Gordeev |
| 3,554,399 A | | 1/1971 | Chapman et al. |
| 3,561,644 A | * | 2/1971 | Works et al. ................ 222/95 |
| 3,677,444 A | | 7/1972 | Merrill |
| 3,685,248 A | | 8/1972 | Godelaine |
| 3,698,595 A | | 10/1972 | Gortz et al. |
| 3,729,032 A | | 4/1973 | Tischlinger et al. |
| 3,811,591 A | | 5/1974 | Novitch |
| 3,820,689 A | | 6/1974 | Cocita |
| 3,921,333 A | | 11/1975 | Clendinning et al. |
| 3,987,938 A | | 10/1976 | Cooprider et al. |
| 3,993,069 A | | 11/1976 | Buckles et al. |
| 4,015,752 A | | 4/1977 | Meuresch et al. |
| 4,023,607 A | | 5/1977 | Jensen et al. |
| 4,048,255 A | | 9/1977 | Hillier et al. |
| 4,078,705 A | | 3/1978 | Butcher |
| 4,099,651 A | | 7/1978 | Von Winckelmann |
| 4,132,334 A | | 1/1979 | Danks |
| 4,168,020 A | | 9/1979 | Benson |
| 4,216,236 A | | 8/1980 | Mueller et al. |
| 4,233,262 A | | 11/1980 | Curto |
| 4,239,132 A | | 12/1980 | Mueller et al. |
| 4,240,465 A | | 12/1980 | Rader |
| 4,249,675 A | | 2/1981 | Nilson |
| 4,250,611 A | | 2/1981 | Wong |
| 4,256,242 A | | 3/1981 | Christine |
| 4,264,018 A | | 4/1981 | Warren |
| 4,314,654 A | | 2/1982 | Gaubert |
| 4,346,708 A | | 8/1982 | LeVeen et al. |
| 4,349,133 A | * | 9/1982 | Christine .............. G01F 11/088 222/183 |
| 4,366,912 A | | 1/1983 | Matakura et al. |
| 4,390,111 A | | 6/1983 | Robbins et al. |
| 4,401,239 A | | 8/1983 | Thomassen |
| 4,416,395 A | | 11/1983 | Gaubert |
| 4,420,100 A | | 12/1983 | Mueller |
| 4,425,366 A | | 1/1984 | Sozzie et al. |
| 4,425,698 A | | 1/1984 | Petrie |
| 4,440,316 A | | 4/1984 | Christine |
| 4,441,538 A | * | 4/1984 | Larkin ...................... A61J 1/10 215/247 |
| 4,444,330 A | | 4/1984 | Kasai et al. |
| 4,457,454 A | | 7/1984 | Meshberg |
| 4,479,989 A | | 10/1984 | Mahal |
| 4,482,585 A | | 11/1984 | Ohodaira et al. |
| 4,493,438 A | | 1/1985 | Rutter |
| 4,499,148 A | | 2/1985 | Goodale et al. |
| 4,501,781 A | | 2/1985 | Kushida et al. |
| 4,516,691 A | | 5/1985 | Christine et al. |
| 4,520,948 A | | 6/1985 | Hampel et al. |
| 4,526,294 A | | 7/1985 | Hirschmann et al. |
| 4,547,900 A | * | 10/1985 | Larkin ...................... A61J 1/10 215/249 |
| 4,561,571 A | | 12/1985 | Chen |
| 4,578,295 A | | 3/1986 | Jabarin |
| 4,579,757 A | | 4/1986 | Su et al. |
| 4,602,725 A | | 7/1986 | Malpas et al. |
| 4,603,066 A | | 7/1986 | Jabarin |
| 4,603,793 A | | 8/1986 | Stern |
| 4,607,764 A | | 8/1986 | Christine |
| 4,636,412 A | | 1/1987 | Field |
| 4,660,737 A | | 4/1987 | Green et al. |
| 4,664,275 A | | 5/1987 | Kasai et al. |
| 4,667,854 A | | 5/1987 | McDermott et al. |
| 4,682,703 A | | 7/1987 | Kasai et al. |
| 4,700,838 A | | 10/1987 | Falciani et al. |
| 4,703,781 A | | 11/1987 | Meyer et al. |
| 4,704,510 A | | 11/1987 | Matsui |
| 4,722,459 A | | 2/1988 | Goncalves |
| 4,747,834 A | | 5/1988 | Prindle |
| 4,760,937 A | | 8/1988 | Evezich |
| 4,776,495 A | | 10/1988 | Vignot |
| 4,784,652 A | | 11/1988 | Wikstrom |
| 4,795,063 A | | 1/1989 | Sekiguchi et al. |
| 4,815,619 A | | 3/1989 | Turner et al. |
| 4,817,830 A | | 4/1989 | Yavorsky |
| 4,823,990 A | | 4/1989 | Roggenburg et al. |
| 4,830,229 A | | 5/1989 | Ball |
| 4,834,152 A | | 5/1989 | Howson et al. |
| 4,842,028 A | | 6/1989 | Kaufman et al. |
| 4,854,481 A | | 8/1989 | Bohl et al. |
| 4,854,483 A | | 8/1989 | Haggart |
| 4,859,513 A | | 8/1989 | Gibbons et al. |
| 4,880,675 A | | 11/1989 | Mehta |
| 4,910,147 A | | 3/1990 | Bacehowski et al. |
| 4,910,435 A | | 3/1990 | Wakalopulos |
| 4,921,733 A | | 5/1990 | Gibbons et al. |

(56) References Cited

U.S. PATENT DOCUMENTS

| | | | |
|---|---|---|---|
| 4,964,540 A * | 10/1990 | Katz | 222/95 |
| 4,981,479 A | 1/1991 | Py | |
| 5,009,654 A | 4/1991 | Minshall et al. | |
| 5,031,675 A | 7/1991 | Lindgren | |
| 5,033,647 A | 7/1991 | Smith et al. | |
| 5,038,839 A | 8/1991 | Morimoto et al. | |
| 5,074,440 A | 12/1991 | Clements et al. | |
| 5,085,332 A | 2/1992 | Gettig et al. | |
| 5,088,612 A | 2/1992 | Storar et al. | |
| 5,088,995 A | 2/1992 | Packard et al. | |
| 5,099,885 A | 3/1992 | Nilsson | |
| 5,100,027 A | 3/1992 | Gueret | |
| 5,102,705 A | 4/1992 | Yammoto et al. | |
| 5,108,007 A | 4/1992 | Smith et al. | |
| 5,129,212 A | 7/1992 | Duffey et al. | |
| 5,145,083 A | 9/1992 | Takahashi | |
| 5,154,319 A | 10/1992 | Deininger et al. | |
| 5,176,510 A | 1/1993 | Nilsson | |
| 5,178,300 A | 1/1993 | Haviv et al. | |
| 5,226,568 A | 7/1993 | Newton et al. | |
| 5,238,150 A * | 8/1993 | Williams | 222/95 |
| 5,238,153 A | 8/1993 | Castillo et al. | |
| 5,263,946 A | 11/1993 | Klug | |
| 5,267,986 A | 12/1993 | Py | |
| 5,271,513 A | 12/1993 | Crosnier et al. | |
| 5,303,851 A | 4/1994 | Libit et al. | |
| 5,320,845 A | 6/1994 | Py | |
| 5,332,121 A | 7/1994 | Schmidt et al. | |
| 5,337,775 A | 8/1994 | Lane et al. | |
| 5,339,972 A | 8/1994 | Crosnier et al. | |
| 5,341,854 A | 8/1994 | Zezulka et al. | |
| 5,360,145 A | 11/1994 | Gueret | |
| 5,366,108 A | 11/1994 | Darling | |
| 5,390,469 A | 2/1995 | Shimizu et al. | |
| 5,401,259 A | 3/1995 | Py | |
| 5,409,146 A | 4/1995 | Hazard et al. | |
| 5,411,065 A | 5/1995 | Meador et al. | |
| 5,414,267 A | 5/1995 | Wakalopulos | |
| 5,419,465 A | 5/1995 | Schroeder | |
| 5,429,254 A | 7/1995 | Christine | |
| 5,435,463 A | 7/1995 | Hodgson | |
| 5,452,826 A | 9/1995 | Stern | |
| 5,453,096 A | 9/1995 | Lataix | |
| 5,454,488 A | 10/1995 | Geier | |
| 5,464,125 A | 11/1995 | Daansen | |
| 5,484,566 A | 1/1996 | Gabbard | |
| 5,492,252 A | 2/1996 | Gueret | |
| RE35,187 E | 3/1996 | Gortz | |
| 5,496,302 A | 3/1996 | Minshall et al. | |
| 5,499,758 A | 3/1996 | McCann et al. | |
| RE35,203 E | 4/1996 | Wakalopulos | |
| D368,774 S | 4/1996 | Py | |
| 5,505,341 A | 4/1996 | Gueret | |
| 5,514,339 A | 5/1996 | Leopardi et al. | |
| 5,549,141 A | 8/1996 | Meador et al. | |
| D374,719 S | 10/1996 | Py | |
| 5,562,960 A | 10/1996 | Sugiura et al. | |
| 5,565,160 A | 10/1996 | Makuuchi et al. | |
| 5,612,588 A | 3/1997 | Wakalopulos | |
| 5,613,517 A | 3/1997 | Handler | |
| 5,613,957 A | 3/1997 | Py | |
| 5,615,795 A | 4/1997 | Tipps | |
| 5,617,976 A | 4/1997 | Gueret | |
| 5,641,004 A | 6/1997 | Py | |
| 5,642,838 A | 7/1997 | Stoody | |
| 5,664,705 A | 9/1997 | Stolper | |
| 5,665,079 A | 9/1997 | Stahl | |
| 5,673,535 A | 10/1997 | Jagger | |
| 5,676,267 A | 10/1997 | Slat et al. | |
| 5,685,869 A | 11/1997 | Py | |
| 5,687,882 A | 11/1997 | Mueller | |
| 5,697,532 A | 12/1997 | Wilde et al. | |
| 5,702,019 A | 12/1997 | Grimard | |
| 5,746,728 A | 5/1998 | Py | |
| 5,772,079 A | 6/1998 | Gueret | |
| 5,780,130 A | 7/1998 | Hansen et al. | |
| 5,803,311 A | 9/1998 | Fuchs | |
| 5,804,236 A | 9/1998 | Frisk | |
| 5,816,772 A | 10/1998 | Py | |
| 5,836,484 A | 11/1998 | Gerber | |
| 5,842,321 A | 12/1998 | Jones | |
| 5,857,595 A | 1/1999 | Nilson | |
| 5,875,931 A | 3/1999 | Py | |
| 5,909,032 A | 6/1999 | Wakalopulos | |
| 5,931,386 A | 8/1999 | Jouillat | |
| 5,934,509 A | 8/1999 | Niss | |
| 5,944,702 A | 8/1999 | Py | |
| 5,971,181 A | 10/1999 | Niedospial, Jr. et al. | |
| 5,971,224 A | 10/1999 | Garibaldi | |
| RE36,410 E | 11/1999 | Meshberg | |
| 5,996,845 A | 12/1999 | Chen | |
| 6,003,733 A | 12/1999 | Wheeler | |
| 6,021,824 A | 2/2000 | Larsen et al. | |
| 6,024,252 A | 2/2000 | Clyde | |
| 6,033,384 A | 3/2000 | Py | |
| 6,050,435 A | 4/2000 | Bush et al. | |
| 6,062,430 A | 5/2000 | Fuchs | |
| 6,068,150 A | 5/2000 | Mitchell et al. | |
| 6,092,695 A | 7/2000 | Loeffler | |
| 6,140,657 A | 10/2000 | Wakalopulos et al. | |
| 6,145,688 A | 11/2000 | Smith | |
| 6,168,037 B1 | 1/2001 | Grimard | |
| 6,170,715 B1 | 1/2001 | Evans | |
| 6,182,698 B1 | 2/2001 | Barak | |
| 6,189,739 B1 | 2/2001 | Von Schuckmann | |
| 6,199,350 B1 | 3/2001 | Brechel et al. | |
| 6,216,916 B1 | 4/2001 | Maddox et al. | |
| 6,254,579 B1 | 7/2001 | Cogger et al. | |
| 6,308,494 B1 | 10/2001 | Yuyama et al. | |
| RE37,471 E | 12/2001 | Jagger | |
| 6,325,253 B1 | 12/2001 | Robinson | |
| 6,343,711 B1 | 2/2002 | Coughlin | |
| 6,343,713 B1 | 2/2002 | Abplanalp | |
| 6,364,864 B1 | 4/2002 | Mohiuddin et al. | |
| 6,382,441 B1 | 5/2002 | Carano | |
| 6,385,943 B2 | 5/2002 | Yuyama et al. | |
| 6,386,395 B1 | 5/2002 | Lunghetti | |
| 6,419,124 B1 | 7/2002 | Hennemann et al. | |
| 6,423,040 B1 | 7/2002 | Benktzon et al. | |
| 6,450,994 B1 | 9/2002 | Boyles et al. | |
| 6,455,093 B1 | 9/2002 | Furrer et al. | |
| 6,471,095 B1 | 10/2002 | Cann | |
| 6,478,196 B2 | 11/2002 | Fuchs | |
| 6,491,189 B2 | 12/2002 | Friedman | |
| 6,505,622 B2 * | 1/2003 | Py | A61M 11/06 128/203.18 |
| 6,506,183 B2 | 1/2003 | Cogger | |
| 6,524,287 B1 | 2/2003 | Cogger | |
| 6,547,108 B2 | 4/2003 | Johanson | |
| 6,561,383 B1 | 5/2003 | Reddy et al. | |
| 6,592,918 B2 | 7/2003 | Kaeser | |
| 6,592,922 B2 | 7/2003 | Furrer et al. | |
| 6,604,561 B2 * | 8/2003 | Py | A61J 1/18 141/329 |
| 6,610,036 B2 | 8/2003 | Branch et al. | |
| 6,662,977 B2 | 12/2003 | Gerber et al. | |
| 6,684,916 B2 * | 2/2004 | Py | A61J 1/18 141/2 |
| 6,695,173 B1 | 2/2004 | Fontana | |
| 6,698,628 B2 | 3/2004 | Mascitelli | |
| 6,742,680 B2 | 6/2004 | Friedman | |
| 6,755,327 B1 | 6/2004 | Hazard et al. | |
| D493,366 S | 7/2004 | Rackwtiz | |
| 6,761,286 B2 | 7/2004 | Py et al. | |
| 6,769,627 B2 | 8/2004 | Carhuff et al. | |
| 6,802,436 B2 | 10/2004 | Drennow et al. | |
| 6,814,265 B2 | 11/2004 | Clifford et al. | |
| 6,883,222 B2 | 4/2005 | Landau | |
| 6,892,906 B2 | 5/2005 | Py et al. | |
| 6,957,752 B2 | 10/2005 | Py et al. | |
| 6,962,275 B2 | 11/2005 | deCler et al. | |
| 6,971,553 B2 | 12/2005 | Brenner et al. | |
| 6,997,219 B2 | 2/2006 | Py et al. | |

(56) References Cited

U.S. PATENT DOCUMENTS

| | | | |
|---|---|---|---|
| 7,000,806 B2* | 2/2006 | Py | A61F 9/0008 222/105 |
| 7,000,960 B2 | 2/2006 | Py | |
| 7,011,233 B2 | 3/2006 | Drennow | |
| 7,032,631 B2* | 4/2006 | Py | B29C 66/7394 141/284 |
| 7,114,635 B2 | 10/2006 | Yamada | |
| 7,278,553 B2 | 10/2007 | Py | |
| 7,290,573 B2 | 11/2007 | Py et al. | |
| 7,322,491 B2 | 1/2008 | Py et al. | |
| 7,328,729 B2 | 2/2008 | Py et al. | |
| 7,357,335 B2 | 4/2008 | Laidler et al. | |
| 7,513,395 B2 | 4/2009 | Labinski et al. | |
| 7,678,089 B2 | 3/2010 | Py et al. | |
| 7,743,948 B2 | 6/2010 | Drennow | |
| 7,789,269 B2 | 9/2010 | Pritchard | |
| 7,806,301 B1 | 10/2010 | Ciavarella et al. | |
| 7,810,529 B2* | 10/2010 | Py | A61L 2/08 141/329 |
| 7,810,677 B2 | 10/2010 | Py et al. | |
| 7,861,750 B2 | 1/2011 | Py et al. | |
| 7,954,521 B2* | 6/2011 | Py | B65D 51/002 141/329 |
| 7,966,746 B2* | 6/2011 | Py | F26B 5/06 34/285 |
| 7,967,034 B2* | 6/2011 | Py | A61L 2/08 141/11 |
| 7,980,276 B2* | 7/2011 | Py | A61J 1/18 141/11 |
| 8,007,193 B2 | 8/2011 | Py et al. | |
| 8,104,644 B2 | 1/2012 | Py et al. | |
| 8,132,600 B2* | 3/2012 | Py | B65D 51/002 141/11 |
| 8,240,521 B2* | 8/2012 | Py | A61F 9/0008 222/1 |
| 8,347,923 B2* | 1/2013 | Py | A61L 2/08 141/11 |
| 8,408,426 B2* | 4/2013 | Bakhos | 222/209 |
| 9,022,079 B2* | 5/2015 | Py | B65D 51/002 141/11 |
| 2001/0027827 A1 | 10/2001 | Jeannin et al. | |
| 2001/0041872 A1 | 11/2001 | Paul, Jr. | |
| 2002/0006353 A1 | 1/2002 | Bilstad et al. | |
| 2002/0010995 A1 | 1/2002 | Thibault et al. | |
| 2002/0018731 A1 | 2/2002 | Bilstad et al. | |
| 2002/0029022 A1 | 3/2002 | Naritomi et al. | |
| 2002/0050301 A1 | 5/2002 | Jeannin et al. | |
| 2002/0071708 A1 | 6/2002 | Fontanet et al. | |
| 2002/0074362 A1 | 6/2002 | Py et al. | |
| 2002/0121527 A1 | 9/2002 | Good | |
| 2002/0124907 A1 | 9/2002 | Crossdale et al. | |
| 2002/0131902 A1 | 9/2002 | Levy | |
| 2002/0172615 A1 | 11/2002 | Woodworth et al. | |
| 2003/0012858 A1 | 1/2003 | Furrer et al. | |
| 2003/0082070 A1 | 5/2003 | Liberto et al. | |
| 2003/0089743 A1 | 5/2003 | Py | |
| 2003/0156973 A1 | 8/2003 | Bilstad et al. | |
| 2004/0011820 A1 | 1/2004 | Abergel et al. | |
| 2004/0112925 A1 | 6/2004 | Py et al. | |
| 2004/0118291 A1 | 6/2004 | Carhuff et al. | |
| 2004/0194811 A1 | 10/2004 | Carhuff et al. | |
| 2005/0029307 A1 | 2/2005 | Py et al. | |
| 2005/0072480 A1 | 4/2005 | Brandes | |
| 2005/0089358 A1 | 4/2005 | Py et al. | |
| 2005/0165368 A1 | 7/2005 | Py et al. | |
| 2005/0260090 A1 | 11/2005 | Stark et al. | |
| 2006/0169722 A1 | 8/2006 | Py et al. | |
| 2006/0186139 A1 | 8/2006 | Laidler et al. | |
| 2009/0224002 A1* | 9/2009 | Bakhos | 222/209 |
| 2011/0297677 A1 | 12/2011 | Py et al. | |
| 2012/0111894 A1* | 5/2012 | Bakhos | 222/209 |
| 2013/0214009 A1* | 8/2013 | Bakhos | 222/209 |

FOREIGN PATENT DOCUMENTS

| | | |
|---|---|---|
| EP | 0172711 | 2/1986 |
| EP | 0616141 | 9/1994 |
| EP | 0649795 | 4/1995 |
| EP | 0733559 | 9/1996 |
| EP | 0743263 | 11/1996 |
| EP | 0 802 827 B1 | 8/1998 |
| EP | 1546021 | 2/2004 |
| FR | 2509689 | 7/1981 |
| FR | 2709733 | 3/1995 |
| GB | 500534 | 2/1939 |
| GB | 984149 | 2/1965 |
| GB | 2091229 | 7/1982 |
| GB | 2364700 | 2/2002 |
| JP | 52-91345 A1 | 7/1977 |
| JP | S59-10986 | 4/1984 |
| JP | 63-156978 | 10/1988 |
| JP | H2-21078 | 6/1990 |
| JP | 2-97427 | 8/1990 |
| JP | 2-111636 U | 9/1990 |
| JP | 06-239379 | 8/1994 |
| JP | 07-125799 | 5/1995 |
| JP | 10-156269 | 6/1998 |
| JP | 11-268778 A | 10/1999 |
| JP | 2002-347812 | 12/2002 |
| JP | 05-016950 | 1/2003 |
| JP | 2005-535530 | 11/2005 |
| WO | WO85/03062 | 7/1985 |
| WO | WO 93/16955 | 9/1993 |
| WO | WO 96/21512 | 7/1996 |
| WO | WO 99/32185 | 1/1999 |
| WO | WO 99/41158 | 8/1999 |
| WO | WO 00/29192 | 5/2000 |
| WO | WO 02/40122 | 5/2002 |
| WO | WO 03/033363 | 4/2003 |
| WO | 2004039690 | 5/2004 |

OTHER PUBLICATIONS

International Search Report for International Application No. PCT/US2003/33503 issued Dec. 1, 2004. 1 page.

\* cited by examiner

FIG. 1
FIG. 1A
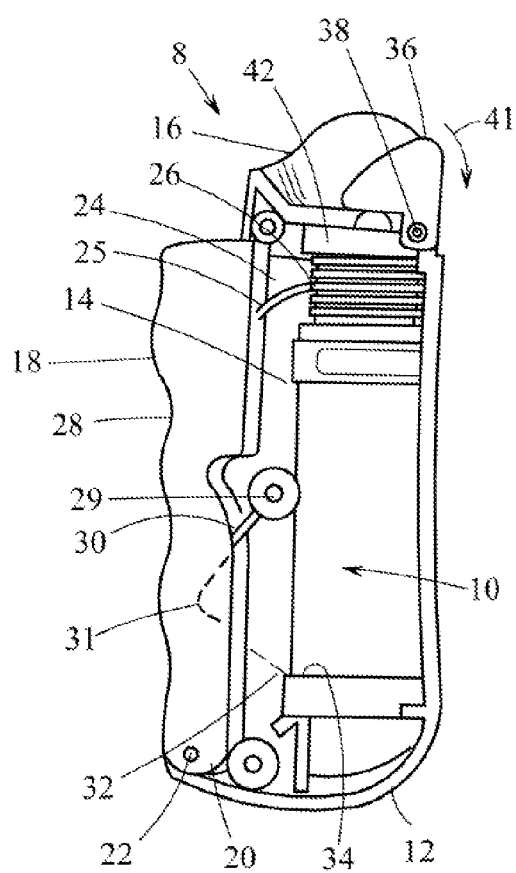
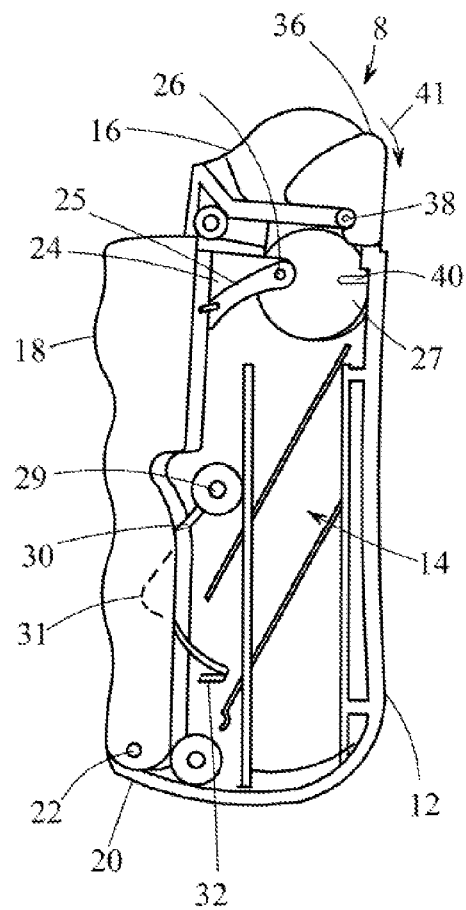

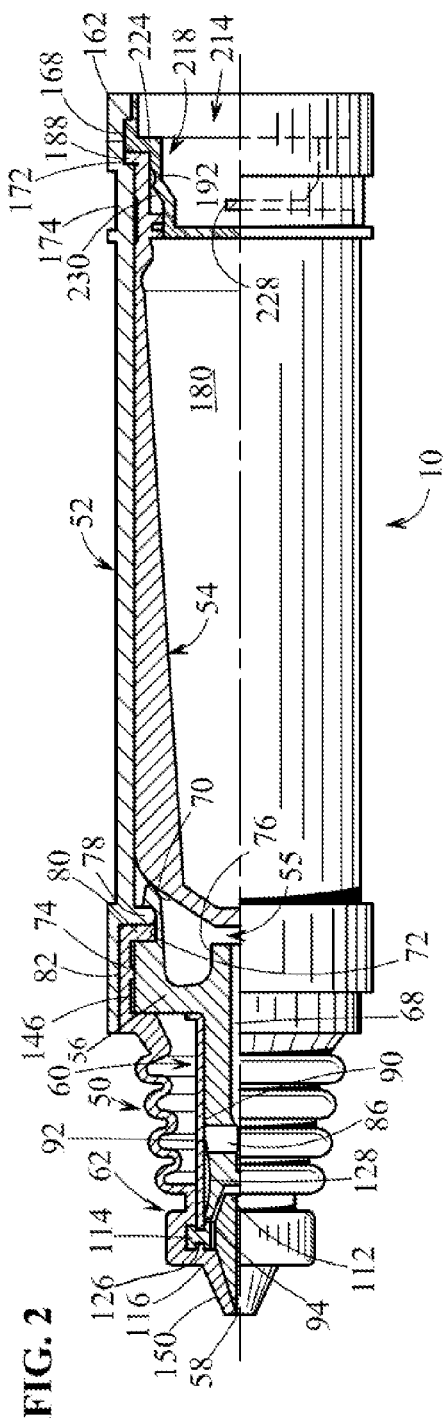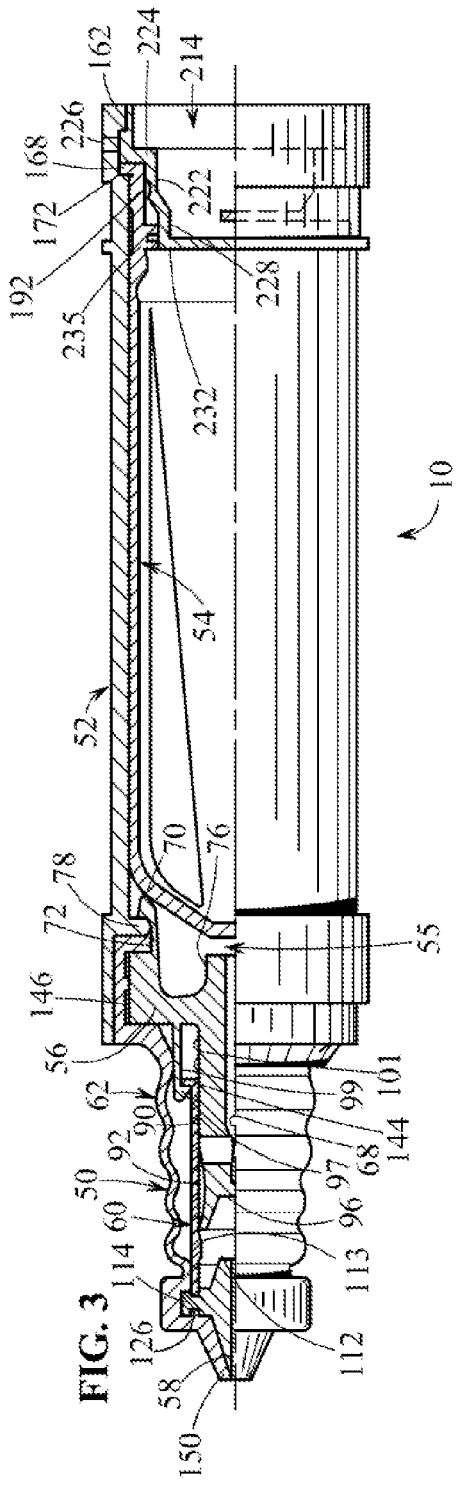

FIG. 7
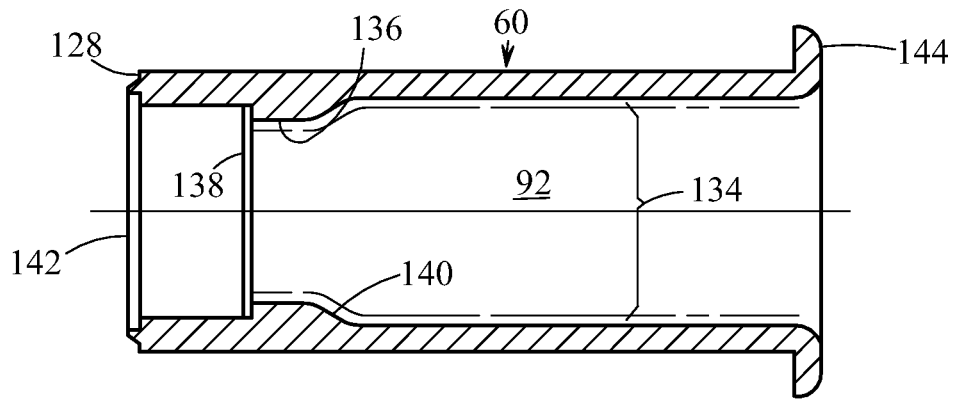
FIG. 8
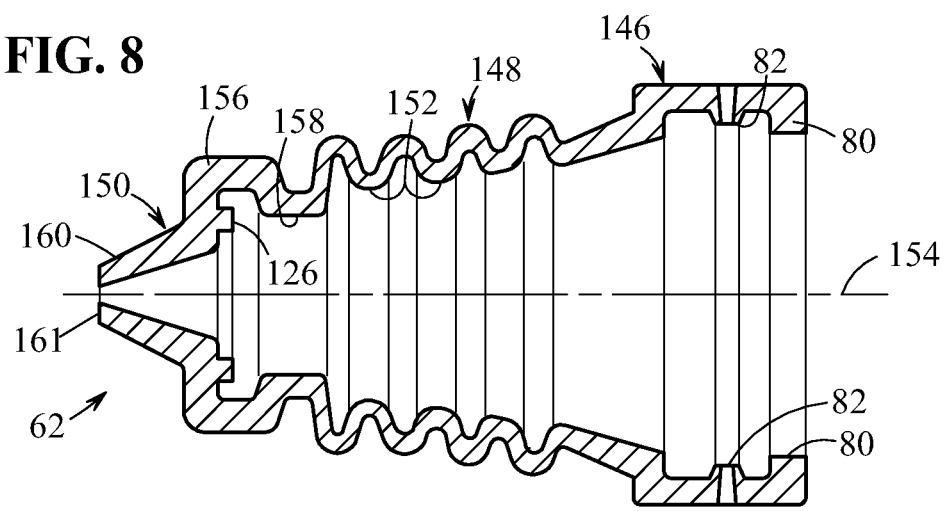
FIG. 9
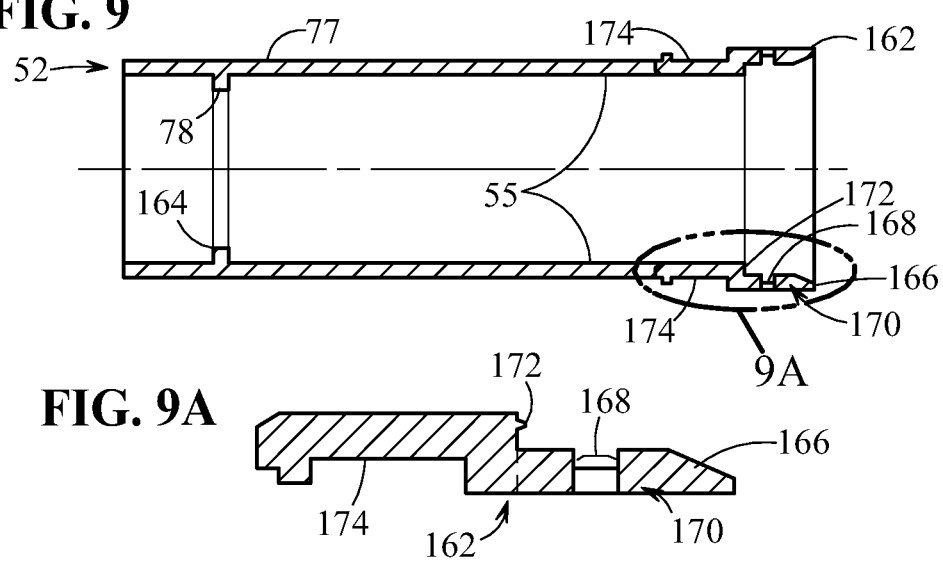
FIG. 9A

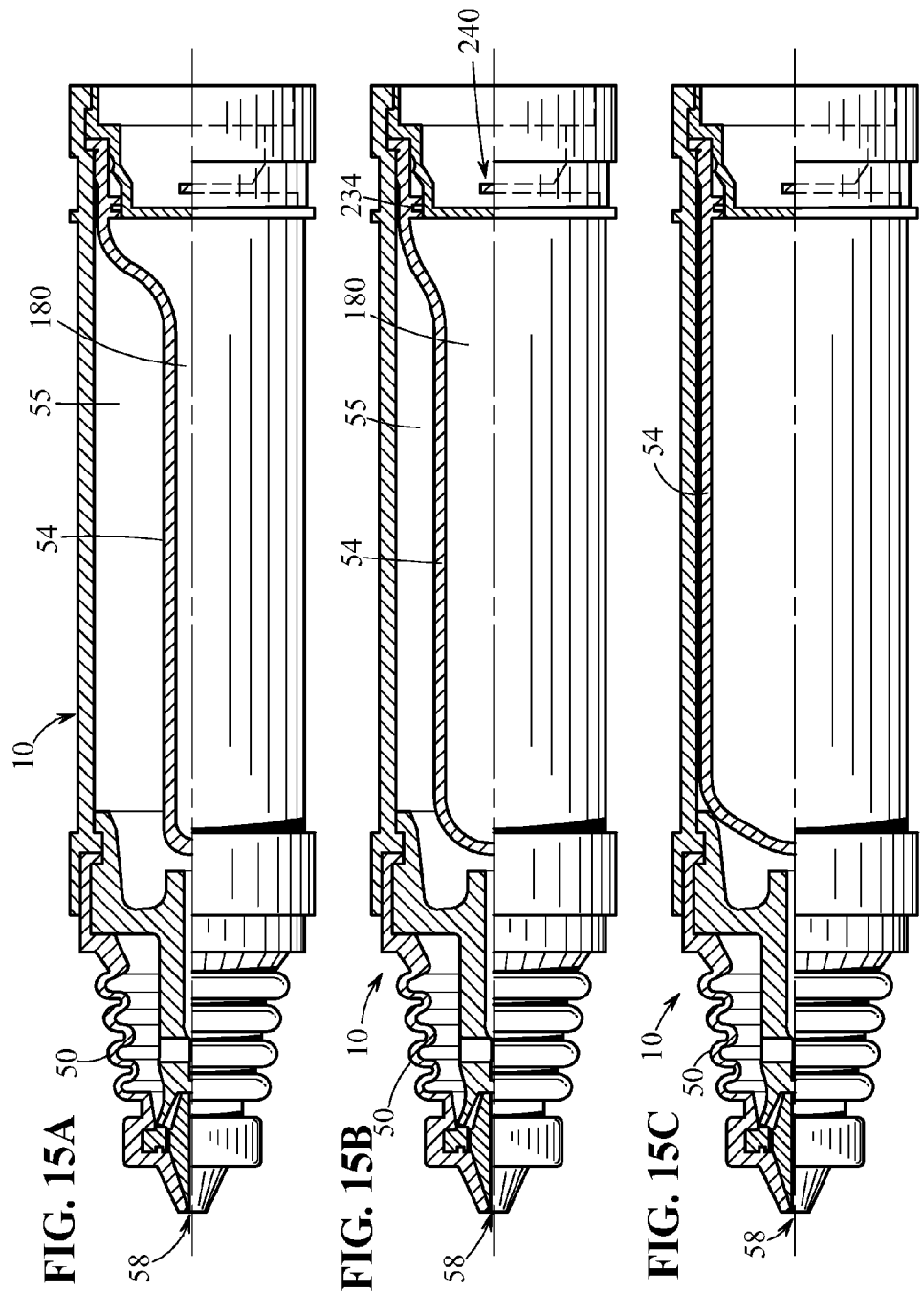

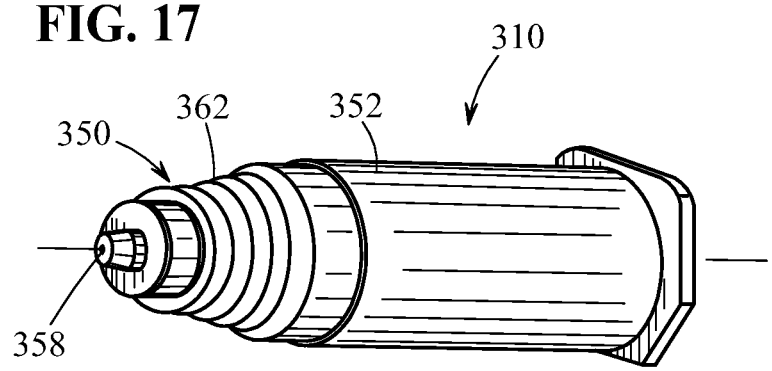
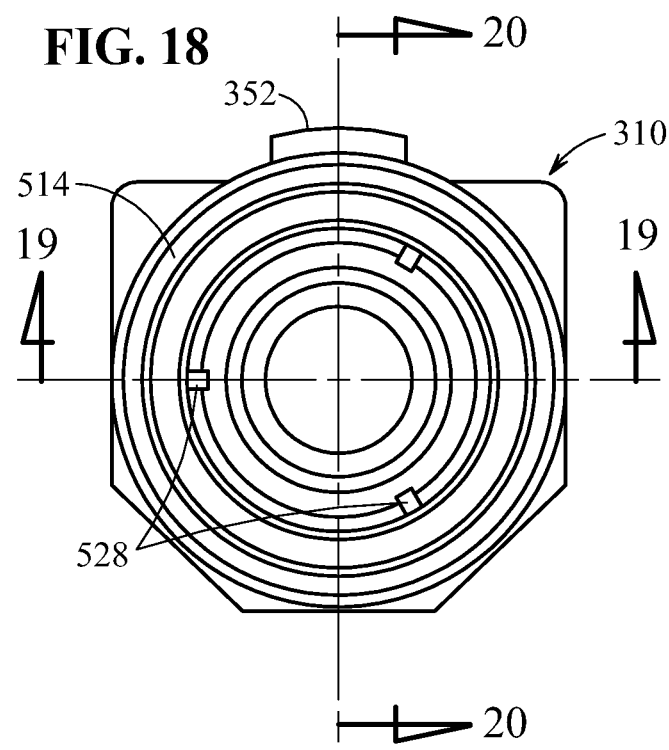

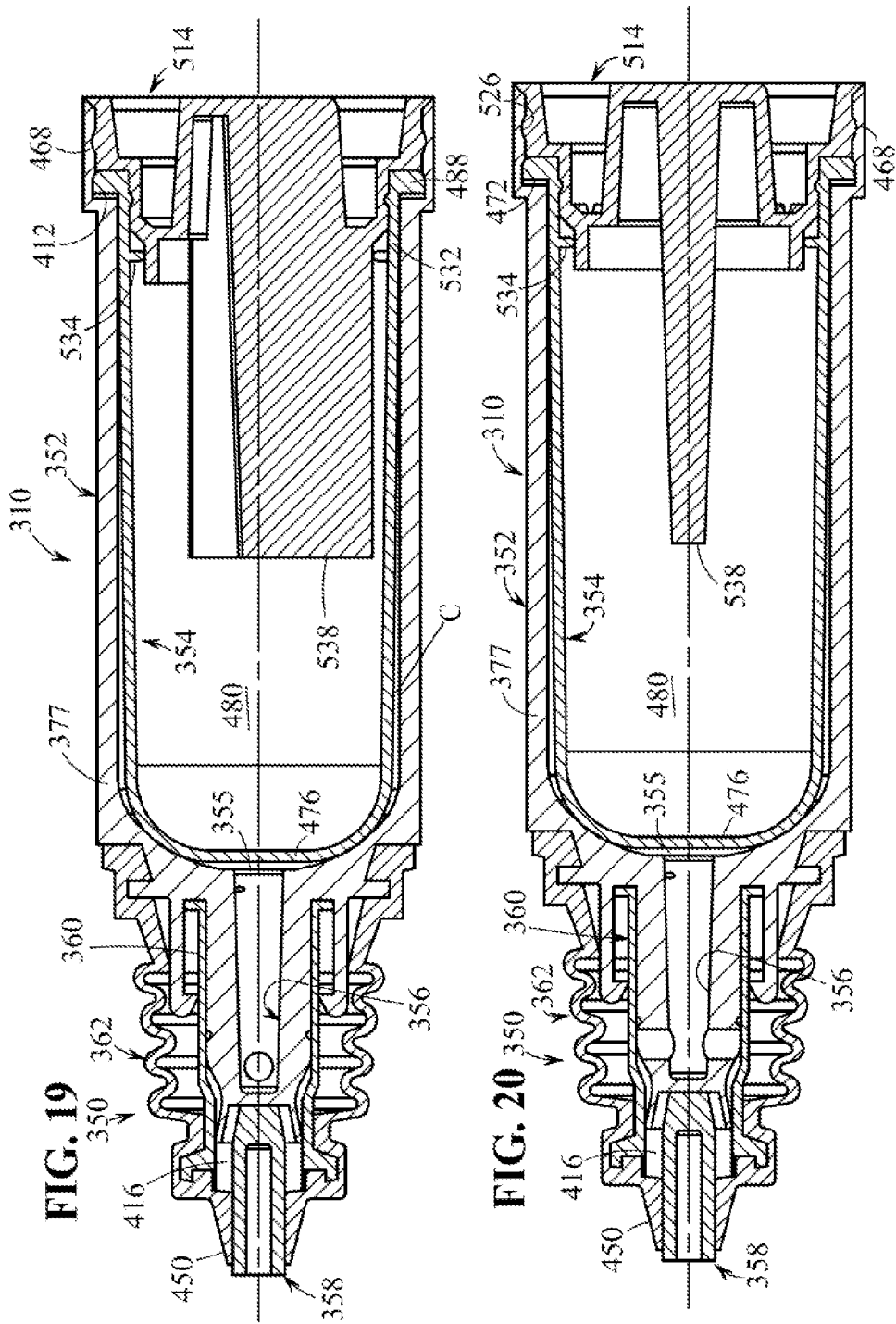

FLUID DISPENSER HAVING A ONE-WAY VALVE, PUMP, VARIABLE-VOLUME STORAGE CHAMBER, AND A NEEDLE PENETRABLE AND LASER RESEALABLE PORTION

CROSS-REFERENCE TO RELATED APPLICATIONS

This patent application is a continuation of U.S. patent application Ser. No. 11/351,716, filed Feb. 10, 2006, now U.S. Pat. No. 8,240,521, entitled "Fluid Dispenser Having a One-Way Valve, Pump, Variable-Volume Storage Chamber, and a Needle Penetrable and Laser Resealable Portion, which is a continuation of U.S. patent application Ser. No. 10/890,465, filed Jul. 12, 2004, now U.S. Pat. No. 7,000,806, entitled "Fluid Dispenser Having a One Way Valve, Pump, Variable-Volume Storage Chamber, and a Needle Penetrable and Laser Resealable Portion", which is a continuation of U.S. patent application Ser. No. 10/001,745, filed Oct. 23, 2001, now U.S. Pat. No. 6,761,286, entitled "Fluid Dispenser Having a Housing and Flexible Inner Bladder", which claims the benefit of U.S. Provisional Application No. 60/242,595, filed Oct. 23, 2000, entitled "Fluid Dispenser Having A Rigid Vial And Flexible Inner Bladder", and U.S. Provisional Application No. 60/242,974, filed Oct. 24, 2000, entitled "Fluid Dispenser Having A Rigid Vial And Flexible Inner Bladder", all of which are hereby incorporated by reference as part of the present disclosure.

FIELD OF THE INVENTION

The present disclosure relates generally to dispensers for dispensing fluids or other substances and, more particularly, to a dispenser having a rigid vial, a flexible bladder disposed within the rigid vial and defining a chamber between the flexible bladder and rigid vial for receiving therein a fluid or other substance, and a nozzle and pump assembly coupled in fluid communication with chamber for dispensing fluids or other substances therefrom.

BACKGROUND INFORMATION

Typical fluid dispensers include a container defining therein a chamber for receiving a fluid to be dispensed, a nozzle and pump assembly mounted on the container, and a dip tube extending downwardly from the nozzle into the chamber for pumping the fluid from the bottom of the chamber, through the dip tube, and out of the dispenser. Other known dispensers include a vial and a flexible bladder received within the vial. For example, U.S. Pat. No. 6,062,430 to Fuchs shows in FIG. 1 a dispensing container with variable volume compensation including a bottle-shaped vessel 2 in the form of a thin-walled, hollow body made from soft elastic plastic, and a reception container 15 formed of a wrinkle film encapsulated within the vessel body 2.

One of the drawbacks associated with typical prior art fluid dispensers is that the fluid chamber(s) are not maintained in a substantially airless condition throughout the storage, shelf life and/or usage of the dispenser. For example, the nozzles and/or valves used in typical prior art dispensers frequently are incapable of maintaining the dispenser in a hermetically sealed condition. Such nozzles and/or valves allow the passage of air or other gases therethrough and into contact with the medicament or other substance contained within the fluid chamber(s). In addition, such nozzles and/or valves frequently allow vapor loss therethrough either during the storage, shelf life or usage of the dispensers.

Another drawback associated with prior art dispensers is that the materials of construction may undergo creep that, in turn, causes seals formed within the dispensers to leak. Many medicaments are maintained in storage and/or on store shelves for at least several, and in some instances, many months. During transportation and storage, the dispensers can be subjected to varying atmospheric conditions involving large variations in atmospheric temperature, pressure and/or humidity. As a result, the dispensers are frequently subjected to substantial differential thermal expansion and/or contraction that, in turn, cause the materials of construction to undergo creep. The seals and other components of such prior art dispensers typically are not designed to address such creep, and as a result, the dispensers develop leaks or otherwise allow air ingress and/or vapor loss when subjected to such long periods of storage or varying atmospheric conditions. For example, some polyethylene dispensers have been known to lose between about 10% to 25% of the weight of their contents during storage. Such weight loss is believed to be due to vapor loss from the medicament or other fluid-containing chambers through the polyethylene walls of the dispensers and/or through leaks otherwise created in the seals or other structural interfaces of the containers. The vapor loss is typically offset by air ingress into the chambers. Vapor loss and/or air ingress is particularly problematic for dispensers containing medicaments, such as pharmaceutical preparations or vaccines, because they tend to dilute each predetermined dosage of the medicament dispensed from the container, and/or cause the dispenser to dispense inconsistent concentrations of medicament from one dose to the next.

Yet another disadvantage associated with prior art dispensers is that because they cannot reliably maintain the medicament or other substance contained therein in an airtight condition, they cannot be used for either multiple dose applications or preservative-free formulations. The use of single dose dispensers can be substantially more expensive than multiple dose dispensers. In addition, the preservatives used in many medicaments, such as pharmaceutical preparations and vaccines, can cause adverse reactions in patients and/or dilute the effect of the medicament on the patient.

Another drawback of prior art dispensers is that the ullage or "dead space" inherent in such dispensers allows sediment build-up. Many medicaments and other formulations contained within such dispensers are suspensions. The ullage or dead space in the prior art dispensers allows the solutes or other solid components of such suspensions to form sediment therein. Such settling of the suspensions dilutes the medicaments or other substances contained within the dispensers and, in turn, alters the medicament and/or the concentration of medicament in each patient dose.

Another drawback associated with many prior art dispensers is that they can only dispense the medicament or other substance contained therein in an upright or other single orientation. This drawback prevents such dispensers from being used effectively in other orientations, such as upside down. In addition, because such dispensers do not maintain the medicament or other substance contained therein in an airless condition, they cannot be used in low gravity environments, such as outer space.

Accordingly, it is an object of the present invention to overcome one or more of the above-described drawbacks and disadvantages of the prior art.

SUMMARY OF THE INVENTION

In accordance with a first aspect, the present invention is directed to a dispenser for dispensing a fluid. The dispenser comprises a rigid housing, and a flexible bladder mounted within the housing and defining an interior chamber within the flexible bladder, and a fluid-receiving chamber between the flexible bladder and the rigid housing. The dispenser further comprises means for creating a first pressure within the fluid-receiving chamber greater than a second pressure within the interior chamber of the bladder to thereby prevent the ingress of gases or vapors into the fluid-receiving chamber. In a currently preferred embodiment of the present invention, the means for creating the pressure differential is formed by a resilient material of the bladder that flexes the bladder outwardly toward an expanded condition, and thereby creates the first pressure within the fluid-receiving chamber greater than the second pressure in the interior chamber of the bladder. Preferably, the resilient bladder is molded in the expanded condition, and therefore the resilient bladder will inherently tend to force itself into the expanded condition and thereby create the desired pressure differential between the fluid-receiving chamber and the interior chamber of the bladder.

A currently preferred embodiment of the dispenser further comprises a pump coupled in fluid communication with the fluid-receiving chamber for pumping a fluid received therein from the dispenser; and a one-way valve coupled in fluid communication with the pump for allowing the passage of the pumped fluid therethrough and preventing the passage of fluids in the opposite direction. The one-way valve is preferably formed by a nozzle, and a flexible cover overlying the nozzle and creating the one-way valve at the interface of the nozzle and cover.

Also in accordance with a preferred embodiment of the present invention, the dispenser further comprises a seal formed between the flexible bladder and the rigid vial for sealing the fluid-receiving chamber. The seal includes a first protuberance extending radially outwardly on an outer surface of the flexible bladder, and a second protuberance axially spaced relative to the first protuberance and extending radially inwardly on an inner surface of the bladder. The first and second protuberances are subject to radial compression to seal the interface between the flexible bladder and rigid vial. Preferably, the first protuberance extends about an outer peripheral surface of the bladder and defines an outer annular sealing surface, and the second protuberance extends about an inner peripheral surface of the bladder and defines an inner annular sealing surface. In addition, the first protuberance defines a tapered surface for directing bladder material in approximately the direction of the second protuberance to thereby facilitate maintaining a fluid-tight seal in the event of bladder material creep. The seal preferably further includes a peripheral flange extending about an open end of the flexible bladder and subject to axial compression for further sealing the interface between the bladder and rigid vial.

Also in accordance with a preferred embodiment of the present invention, the dispenser further comprises a plug receivable within an open end of the rigid vial and engageable with at least one of the first and second protuberances for radially compressing the protuberances to seal the interface between the flexible bladder and rigid vial. The plug defines at least one aperture therethrough in fluid communication with the interior chamber of the flexible bladder. Preferably, a two-way valve of the dispenser is coupled in fluid communication between the interior chamber of the flexible bladder and the aperture of the plug for preventing fluid communication between the interior chamber of the bladder and the ambient atmosphere when a pressure differential across the two-way valve is less than a threshold level. The two-way valve preferably is formed by a flexible, annular protuberance extending radially inwardly from an inner peripheral surface of the flexible bladder, and engageable with an annular surface of the plug to thereby seal the interface between the flexible bladder and plug. In a currently preferred embodiment of the present invention, the annular protuberance defines axially-opposed surfaces that taper inwardly in the radial direction to facilitate flexing of the protuberance in response to the pressure differential across the protuberance exceeding the predetermined threshold level.

The flexible bladder of the dispenser further defines an open end and a closed end, and is movable between a collapsed condition and an expanded condition. Upon expansion of the flexible bladder from the collapsed condition into the expanded condition, the flexible bladder and rigid vial define an annular gap therebetween. In a currently preferred embodiment, the annular gap defines an increasing width in the axial direction from the open end toward the closed end of the flexible bladder, to facilitate removal of fluid from the fluid-receiving chamber upon expansion of the bladder. Preferably, the flexible bladder initially contacts the rigid vial adjacent to or near the open end of the bladder, and then progressively engages the rigid vial in the axial direction from the open end toward the closed end of the flexible bladder with further expansion thereof. Also in accordance with a preferred embodiment of the dispenser, the flexible bladder defines an external morphology in an expanded condition, the rigid vial defines an internal morphology, and the external and internal morphologies are substantially the same to thereby allow the flexible bladder to conformably contact the rigid vial and substantially eliminate any dead space in the fluid-receiving chamber therebetween.

In accordance with a preferred embodiment of the present invention, the pump of the dispenser comprises a piston, and a slide for slidably receiving the piston therein. At least one of the piston and the slide is reciprocable relative to the other. In addition, the piston is made of a relatively hard material, the slide is made of a relatively soft material, and the piston causes a compression zone of the slide to flex outwardly upon moving at least one of the piston and the slide relative to the other to thereby effect a fluid-tight seal between the piston and slide. In addition, forming the slide from a relatively flexible material allows the slide to be formed integral with a nozzle, such as by molding the two components in a single part, wherein the integral nozzle and slide may be released from a core pin by injecting pressured air therebetween.

Also in accordance with a preferred embodiment of the present invention, the dispenser preferably further comprises means for controlling the flexible bladder to collapse into a predetermined collapsed condition. In one embodiment of the present invention, the means for controlling includes a plurality of legs extending axially inwardly into the interior chamber of the flexible bladder for conformably contacting the flexible bladder upon collapse thereof. In another embodiment of the present invention, the means for controlling is defined by at least one axially elongated surface discontinuity formed in the flexible bladder.

In accordance with another aspect of the present invention, the dispenser includes a needle penetrable and laser resealable member that is capable of being penetrated by a needle or like injection member for introducing a predetermined substance into the fluid-receiving chamber. In one such embodiment, the flexible bladder includes a first portion substantially infusible in response to the application of thermal energy thereto and compatible with the substance to be received within the fluid-receiving chamber, and a second portion overlying the first portion and fusible in response to the application of thermal energy thereto. Thus, the second portion enables the formation of a substantially fluid-tight seal between the flexible bladder and fluid-receiving chamber in a region thereof penetrated by the needle or like injection member. In one embodiment of the present invention, the second portion is formed of either a thermoplastic or an elastomeric material, and the bladder, including the first portion thereof, is formed of vulcanized rubber.

One advantage of the currently preferred embodiments of the dispenser is that the pressure differential between the fluid-receiving chamber and the internal chamber of the bladder and ambient atmosphere substantially prevents the ingress of air or other gases or vapors through the flexible bladder, or otherwise into the fluid-receiving chamber. As a result, the dispensers of the present invention may maintain the medicaments or other substances contained therein in an airless condition throughout substantial periods of storage, shelf life and/or use. Accordingly, the dispensers of the present invention are particularly well suited for dispensing multiple doses of non-preserved medicaments or other substances requiring storage in an airless condition.

Another advantage of the currently preferred embodiments of the dispensers is that the seal formed between the flexible bladder and the rigid vial radially and axially directs the material of the flexible bladder to persistently maintain a fluid-tight seal regardless of any creep of the material during the storage or shelf-life of the dispenser. In addition, the one-way valve employed in the preferred embodiments of the present invention further maintains the fluid-receiving chamber in a hermetically-sealed condition throughout the storage, shelf-life and/or use of the dispenser.

Yet another advantage of the currently preferred embodiments of the dispensers is that because the medicament or other substance is maintained in an airless condition in the fluid-receiving chamber, the dispensers may be used in virtually any orientation, and furthermore, may be used in low gravity environments.

Another advantage of the dispensers of the present invention is that the flexible bladder preferably defines an external morphology substantially matching the internal morphology of the rigid vial. As a result, the flexible bladder may expand and conformably contact the rigid vial throughout the interface between these two parts and, in turn, eliminate any dead space within the fluid-receiving chamber.

Yet another advantage of the currently preferred embodiments of the dispensers is that the two-way valve coupled in fluid communication between the interior chamber of the flexible bladder and the ambient atmosphere prevents any exchange of gases or vapors between the interior chamber of the bladder and ambient atmosphere, provided the pressure differential across the valve is less than a predetermined level. As a result, the two-way valve creates a relatively stable micro-atmosphere within the interior chamber of the flexible bladder, thus insulating the interior chamber from fluctuations in pressure and/or humidity in the ambient atmosphere and thereby further preventing the ingress of gas or vapors into the fluid-receiving chamber.

Other objects and advantages of the present invention and/or the currently preferred embodiments thereof will become apparent in view of the following detailed description and accompanying drawings.

BRIEF DESCRIPTION OF THE DRAWINGS

FIG. 1 is a partially broken-away, perspective view of an ocular treatment apparatus having a dispenser mounted therein in accordance with a preferred embodiment of the present disclosure.

FIG. 1A is a view similar to FIG. 1 absent the dispenser.

FIG. 2 is a side elevational view, partly in section, illustrating in further detail the dispenser of FIG. 1 including the pump assembly, vial and a bladder and wherein the pump assembly is disposed in a closed position.

FIG. 3 is a view similar to that of FIG. 2, although the dispenser is rotated 90° with respect to its orientation in FIG. 2, and the pump assembly is disposed in an extended position.

FIG. 7 is a central cross-sectional view taken along a longitudinal axis of a slide or body of the pump assembly of FIGS. 2 and 3 and forming essentially the compression zone.

FIG. 8 is a central cross-sectional view taken along a longitudinal axis of a flexible pump cover of the pump assembly of FIGS. 2 and 3, and illustrating the manner in which the pump cover extends from the tip of the nozzle to the rigid vial and is configured to allow reciprocal movement of the piston connected to the vial.

FIG. 9 is a central, cross-sectional view taken along a longitudinal axis of the rigid vial of the dispenser of FIGS. 2 and 3.

FIG. 9A is an enlarged view of a portion of the vial of FIG. 9 showing a rear mounting portion for receiving the bladder of FIG. 10.

FIGS. 15A-C are sequential side elevational views, partly in section, showing the reduction in volume of fluid and corresponding expansion of the bladder in the full, half-full and empty conditions of the dispenser of FIG. 1, respectively.

FIG. 17 is a perspective view of another embodiment of a dispenser of the present disclosure.

FIG. 18 is an end elevational view of the dispenser of FIG. 17.

FIG. 19 is a cross-sectional view of the dispenser of FIGS. 17 and 18 taken along line 19-19 of FIG. 18.

FIG. 20 is a cross-sectional view of the dispenser of FIGS. 17 and 18 taken along line 20-20 of FIG. 18.

DETAILED DESCRIPTION OF THE PREFERRED EMBODIMENTS

Figure 1B:
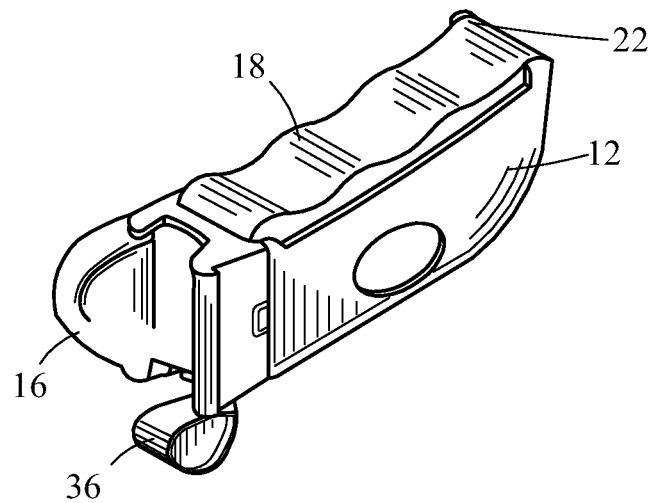
FIG. 1B is a perspective view of the ocular treatment apparatus of FIG. 1.
Figure 1D:
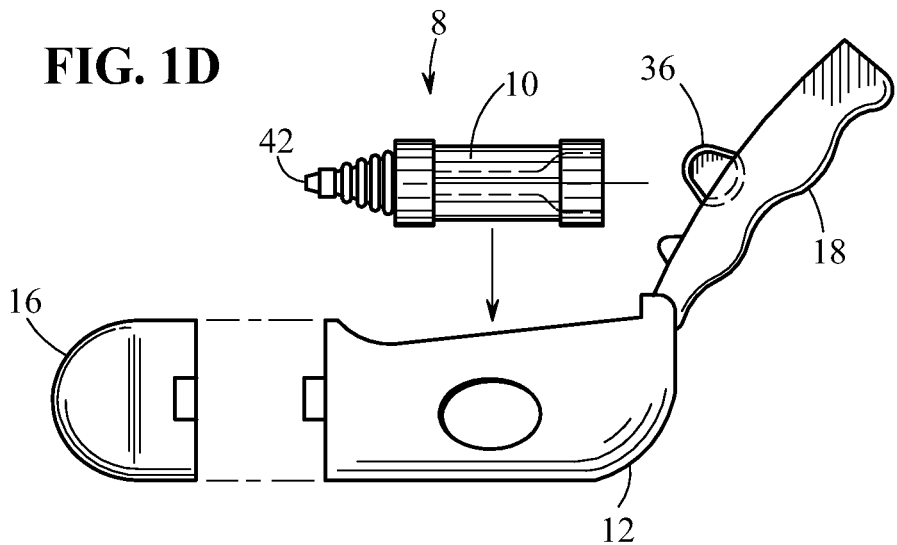
FIG. 1D is an exploded view, in side elevation, of the ocular treatment apparatus of FIG. 1B.
Figure 1C:
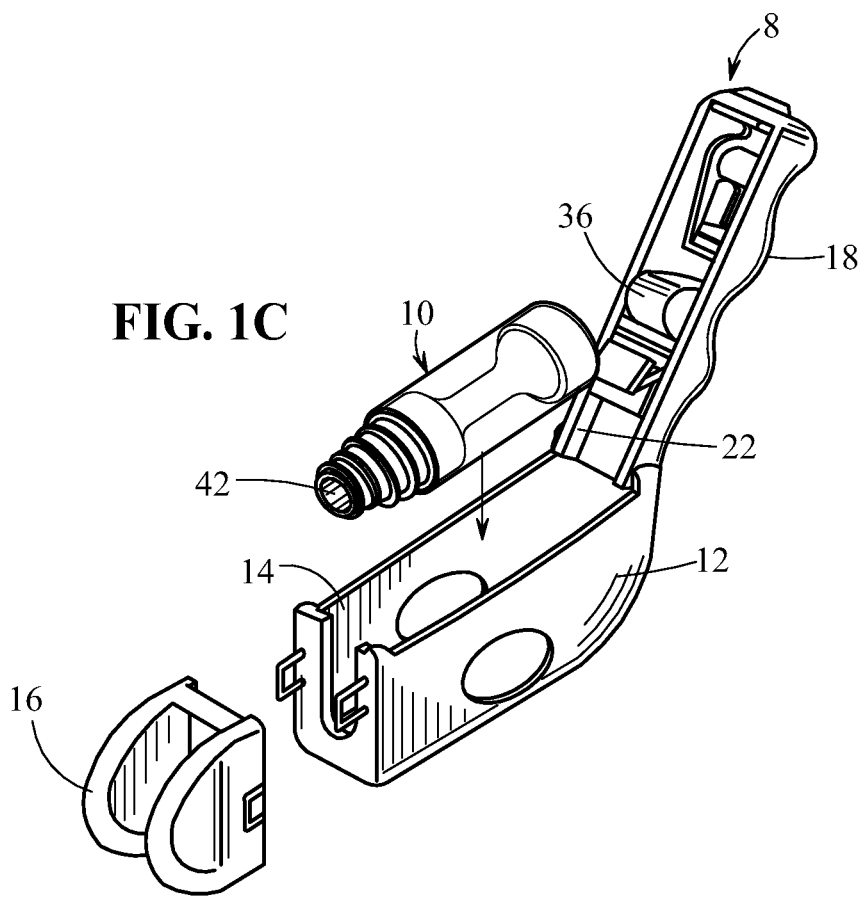
FIG. 1C is an exploded view, in perspective, of the ocular treatment apparatus of FIG. 1B.

In FIG. 1, there is shown an ocular treatment apparatus 8 that may be used in conjunction with a dispenser, shown generally at 10, in accordance with the present disclosure. As seen in FIGS. 1 and 1A, the treatment apparatus 8 comprises a housing 12 that may be generally U-shaped in cross section, and defines an interior cavity 14 and an eye cover 16. A trigger 18 is pivotally connected at one end 20 to the housing 12 via a hinge 22, and includes at the other end an arm portion 24 defining a slot 25. As shown best in FIG. 1A, a pin 26 of a wheel 27 is fixedly secured within the slot 25, and the wheel 27 is rotatably mounted on the interior wall of the housing 12. As best seen in FIG. 1, the trigger 18 is elongated and comprises finger grooves 28 for a comfortable fit with, e.g., a patient's hand. An approximately L-shaped spring arm 30 is fixedly secured at one end to a post 29 projecting inwardly from the interior wall of the housing 12, and the spring arm defines a knee or bent portion 31 (shown in phantom) engaging an interior surface of the trigger 18, and a free end 32 engageable with a rim 34 formed at one end of the dispenser 10. An eyelid depressor 36 is pivotally mounted by a hinge 38 to the end of the housing 12 adjacent to the eye cover 16, and includes a hook 40 fixedly secured to the wheel 27 for pivotally moving the eyelid depressor upon actuating the trigger 18.

In use, the eye cover 16 is placed adjacent to the tissue surrounding the eye with the eyelid depressor 36 engaging the tissue adjacent to the ocular cul-de-sac. Upon squeezing the trigger 18, the eyelid depressor 36 rotates in the direction of the arrow 41, and in turn moves the tissue adjacent to the eye to expose the ocular cul-de-sac. Rotation of the eyelid depressor 36 is caused by the wheel 27 which also uncovers a nozzle 42 formed at the adjacent end of the dispenser 10. Simultaneously, the spring arm 30 forces the rim 34 of the dispenser 10 away from the fixed nozzle 42 to thereby prime the pump of the dispenser, as described in further detail below. Upon squeezing the trigger 18 and correspondingly extending the dispenser 10 within the housing 12, the free end 32 of the spring arm 30 eventually disengages itself from the rim 34 of the dispenser to thereby release the extended dispenser from the spring arm. As a result, due to the resiliency or spring-like nature of the nozzle 42, as described further below, the extended dispenser contracts or moves back toward the nozzle and, in turn, releases a predetermined dosage of medicament (or other substance) from the nozzle and into the ocular cul-de-sac of the user's eye. Then, when the user removes the ocular treatment apparatus 8 from his or her eye and releases the trigger 18, the spring arm 30 automatically returns to its original or resting position as shown in FIG. 1 with the free end 32 engaging the rim 34. The force exerted by the spring arm 30 upon returning to its original position also rotatably drives the wheel 27 in the direction opposite that of the arrow 41 and, in turn, causes the eyelid depressor 36 to return to its original position, as shown. The ocular treatment apparatus is then ready to dispense another predetermined dosage of medicament or other liquid contained therein.

Other examples of ocular treatment apparatus that may employ the dispenser 10 are described in U.S. Pat. Nos. 4,981,479 and 6,033,384, which are assigned to the assignee of the present invention and are hereby incorporated by reference as part of the present disclosure. Accordingly, as may be recognized by those of ordinary skill in the pertinent art based on the teachings herein, the dispensers of the present invention may be utilized in any of numerous different apparatus or systems to facilitate holding and dispensing medicaments or other fluids, liquids or other substances contained therein, such as nasal inhalers.

Referring now to FIGS. 2 and 3, the dispenser 10 is shown partly in cross section to illustrate the internal components thereof. The dispenser 10 is generally cylindrical in outer configuration and comprises a pump assembly 50, a generally rigid vial 52, and a flexible bladder 54 disposed within a main fluid chamber 55 of the vial. The pump assembly 50 comprises a piston 56 for discharging predetermined doses of medicaments or other substances contained within the fluid chamber 55, a slide or body 60 for slidably receiving therein the piston and defining a predetermined dosage chamber therebetween, and a pump cover 62 forming with a nozzle 58 a one-way valve at the dispensing tip and a spring-like bellows for allowing either the piston or nozzle to be moved toward the other to eject a dose of medicament or other substance through the nozzle, and to force either the piston or the nozzle away from the other upon releasing the predetermined dose. The nozzle 58 hermetically seals the dispensing tip of the dispenser and ejects the pumped medicament or other substance therethrough.

Figure 4:
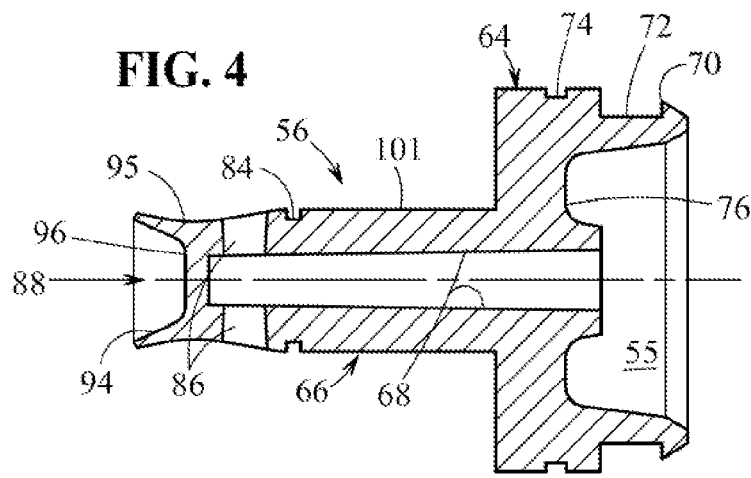
FIG. 4 is a central cross-sectional view taken along a longitudinal axis of a piston of the pump assembly of FIG. 1.

Referring now also to FIG. 4, the piston 56 may be composed of any durable and moldable material, such as a plastic substance and, preferably, the material is suitable for use in connection with medicaments. A suitable material is a low density polyethylene. The piston 56 comprises a base portion 64, an elongated portion 66 extending from the base portion 64, and a central bore 68 which is in fluid communication with the main fluid chamber 55. The base portion 64 is generally disc-like in outer configuration, and comprises a connecting flange 70, an annular mounting portion 72, a first annular groove 74, and a second annular groove 76 spaced inwardly relative to the first annular groove and surrounding the inlet end of the central bore 68. The connecting flange 70 is configured to engage, e.g., in a snap-lock manner, the vial 52 defining a correspondingly dimensioned mounting flange 78 (FIG. 2). As shown in FIG. 2, the mounting portion 72 and first annular groove 74 receive an annular flange 80 and rib 82, respectively, of the pump cover 62 which is composed of a flexible material, as discussed in more detail below, and which thereby seals the main fluid chamber 55 of vial 52. As further shown in FIG. 2, when the piston 56 is assembled to the vial 52, the second annular groove 76 is located adjacent to the main fluid chamber 55. The second annular groove 76 thereby functions to provide a capture area to receive any gas bubbles improperly disposed within the main fluid chamber and to prevent the bubbles from passing into the central bore 68.

As shown best in FIG. 4, the elongated portion 66 comprises an annular groove 84, a laterally-extending bore 86, and a terminal end defining a receptacle portion 88. The annular groove 84 is configured to receive a seal 90 (FIG. 2), such as an o-ring, for sealing the piston in contact with the slide 60. The laterally extending bore 86 is in fluid communication with the central bore 68 and terminates adjacent to an annular interior surface 92 of the slide 60 (FIG. 3). As shown best in FIG. 4, the receptacle portion 88 comprises an annular wall 94, a tapered portion 95 extending between the annular wall 94 and bore 86, and a piston surface 96 for stopping movement of the nozzle 58 as described in more detail below in connection with FIGS. 5 and 6. The annular wall 94 defines a generally increasing outer diameter toward the distal end, and slidably engages the annular interior surface 92 of the slide 60 as described in more detail below in connection with FIG. 7.

As shown in FIG. 3, the piston 56 further includes two generally symmetrically-located hook portions 97, and each hook portion 97 defines in combination with an outer surface 101 of the piston 56 a respective slot 99. As described in more detail below in conjunction with FIG. 7, the slide 60 is reciprocally disposed within the slots 99 for allowing relative movement of the piston within the slide upon actuation of the pump.

Figure 5:
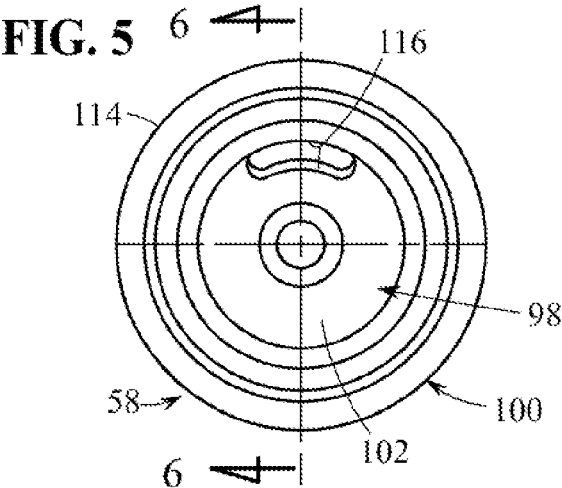
FIG. 5 is a front elevational view of a tip of a nozzle of the pump assembly of FIG. 1.
Figure 6:
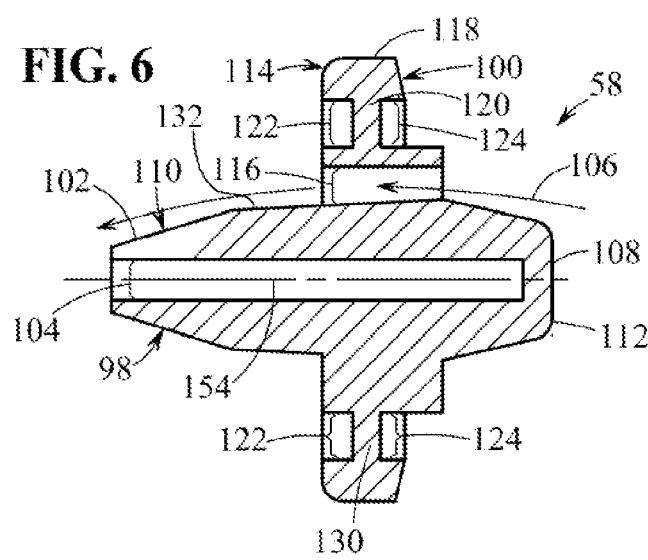
FIG. 6 is a longitudinal cross-sectional view taken along line 6-6 of FIG. 5.

Referring now to FIGS. 5 and 6, the nozzle 58 may be composed of any suitably durable, moldable, somewhat flexible material (in the configuration wherein the nozzle and body are made of one piece), such as a plastic material, and currently is composed of a material which has been found to be compatible with medicaments, such as those materials sold under the trademarks VELEX and LEXAN, both owned by the General Electric Company of Pittsfield, Mass. The nozzle 58 is preferably molded of one piece and comprises a truncated, conical-shaped body portion 98, and a disc portion 100 disposed coaxially with the conical-shaped portion and extending radially therefrom. It will be recognized that the conical-shaped portion 98 and disc portion 100 may be molded together or separately. The conical-shaped portion 98 comprises a tapered outer surface 102, a partial central bore 104, and an engagement portion 106. The partial central bore 104 terminates at a lever wall 108 which is dimensioned and configured to allow flexing of the tapered outer surface 102 in the direction of the arrow 110. The engagement portion 106 is configured to mate with the receptacle portion 88 of the piston 56, described above in connection with FIG. 4, and comprises a truncated conical configuration terminating in an engagement surface 112. As illustrated in FIGS. 2 and 3, when the piston 56 reaches the end of its stroke upon dispensing a predetermined dose, the engagement surface 112 of the nozzle is received within the guide wall 94 and engages the piston surface 96 to terminate further movement. It will be recognized that a variable stroke volume 113 is defined between the engagement surface 112 of the nozzle 58 and the piston surface 96 of the piston 56. As illustrated in FIG. 3, the maximum stroke volume is defined by the maximum extension of the engagement surface 112 from the piston surface 96.

As shown in FIG. 6, the disc portion 100 comprises an annular mounting portion 114 for affixably mounting the nozzle 58 to the pump cover 62 and slide 60 (FIGS. 2 and 3), and also comprises a slot 116 for the passage of fluid or other substances therethrough. The mounting portion 114 comprises an annular thickened portion 118 and a neck portion 120 disposed between a pair of annular grooves 122 and 124. As shown in FIGS. 2 and 3, the annular groove 122 is configured to engage a rib 126 of the pump cover 62 (FIG. 8), and the annular slot 124 is configured to engage a correspondingly configured terminal end portion 128 of the slide 60 (FIG. 7). As shown in FIG. 6, the annular groove 124 defines an annular crevice 130, employed, e.g., for easing assembly of the slide 60 to the nozzle 58. The slot 116 is disposed adjacent to a flattened portion 132 of the tapered outer surface 102, and provides fluid communication from the variable stroke volume 113 through the disc portion 100 to the tapered outer surface.

As illustrated in FIG. 7, the slide 60 defines a tubular body and may be composed of a similar substance to that described above with respect to the nozzle 58 (FIGS. 5 and 6). As described above and referring also to FIG. 2, the slide 60 comprises an annular inside surface 92 within which the piston 56 and engagement portion 106 of the nozzle 58 are disposed after assembly of the dispenser 10. The inside surface 92 defines a bore 134 with a neck portion 136 of reduced diameter disposed between a first transition zone 138 of relatively rapid increase in diameter, and a second transition zone 140 of relatively gradual increase in diameter. Referring now to FIG. 2, it will be understood that during relative movement of the nozzle 58 and the slide 60 away from the piston 56, the annular wall 94 of the piston (FIG. 4) will engage the second transition zone 140 (FIG. 7) in sealing engagement to thereby force fluid contained within the variable stroke volume 113 into the slot 116 of the nozzle tip.

With reference to FIG. 7 and as described above in connection with FIGS. 5 and 6, the slide 60 defines a terminal end 128 that includes an annular ridge 142 configured to engage the crevice 130 of the nozzle 58. As shown in FIG. 3, the opposite end of the slide 60 defines a flange 144 that is configured to engage the hook portion 97 of the piston 56.

FIG. 8 depicts a cross-sectional view of the flexible pump cover 62. The flexible pump cover 62 may be composed of any durable, resilient and flexible material, such as an elastomeric material. Preferably, the pump cover 62 is composed of a thermo-elastic material, such as a styrene-butadiene elastomer sold under the trademark KRATON by GLS of Illinois. Other suitable materials include polyvinyl-chloride, Santoprene™ and butyl rubber. The pump cover 62 comprises a mounting portion 146, a bellows portion 148, and a nozzle cover 150 which cooperates with the slot 116 (FIG. 6) to provide an elastic valve, as described further below in connection with FIG. 5. As described above in connection with FIG. 4, the mounting portion 146 comprises an annular flange 80 that fits within the mounting groove 72 adjacent to the mounting flange 78 of the vial 52 (FIG. 2). As shown in FIG. 8, the rib 82 defines in cross section a truncated conical shape corresponding to the configuration of the annular groove 74 of the piston (FIG. 4). Because of the resilient nature of the material of the pump cover 62, the annular flange 80 may be slightly oversized in order to provide a resilient fit with the vial 52 and piston 56 and thereby, in combination with the rib 82, hermetically seal the main fluid chamber 55 (FIG. 2).

The bellows portion 148 extends between the mounting portion 140 and nozzle cover 150, and comprises a plurality serpentine or inversely curled portions 152 which function to provide resiliency in a direction generally parallel to a central axis 154 and sufficient spring-like force to either drive the piston or the nozzle away from the other and return the piston to the top of its stroke upon dispensing a predetermined dose of a medicament or other substance contained within the chamber 55. Referring also to FIGS. 2 and 6, the nozzle cover 150, when mounted, is dimensioned and configured to resiliently engage the nozzle 58 and slide 60, and includes the annular rib 126 extending axially from a disc engagement portion 156. The disc engagement portion 156 is disposed between a slide engagement portion 158 and a nozzle body engagement portion 160. Referring also to FIG. 6, the nozzle body engagement portion 160 is configured to engage the tapered outer surface 102 of the nozzle 58 to thereby form a normally-closed, one-way valve therebetween. As can be seen in FIG. 8, the cross-sectional thickness of the nozzle engagement portion 160 gradually decreases in the axial direction from the disc engagement portion 156 toward the dispensing tip 161. The gradually-decreasing cross-sectional thickness of the nozzle engagement portion 160 facilitates the release of the medicament or other substance through the one-way valve formed by the elongated, annular interface between the relatively flexible nozzle engagement portion 160 of the cover and the tapered surface 102 of the nozzle body, while simultaneously preventing air or other gases from passing through the valve in the opposite direction, in accordance with the teachings of the below-mentioned patents incorporated by reference herein.

In operation, as described above in connection with FIGS. 1 and 1A, movement of the vial 52 in the axial direction causes the piston 56 to move from the position shown in FIG. 2 into the position shown in FIG. 3 (or vice versa), e.g., by actuating the trigger 28 of FIG. 1 or other actuator, which draws fluid into the variable volume fluid chamber 113 from the main fluid chamber 55 via the central bore 68 and laterally-extending bore 86 of the piston. Referring now also to FIGS. 6 and 8, as the piston 56 moves toward the nozzle 58 (or vice versa), the fluid is injected through the slot 116 (FIG. 6), along the flattened surface 132, between the tapered surface 102 and nozzle body engagement portion 160, and then outwardly of the nozzle tip. Further details of pump assemblies that may be used in the practice of the present invention are described in U.S. Pat. Nos. 5,944,702, 5,875,931 and 5,746,728, which are assigned to the same assignee as the present invention, and are hereby expressly incorporated by reference as part of the present disclosure.

One advantage of the pump configuration of the illustrated embodiment, and as indicated by the arrow indicating the path of fluid flow in FIG. 6, the pumped fluid follows a fairly straight path extending in a direction parallel to the axis 154 from the variable stroke volume 113, over the tapered surfaces of the engagement portion 106, through the slot 116, and between the one-way valve formed by the interface of the nozzle engagement portion 160 of the cover and the tapered outer surfaces 132 and 102 of the nozzle body. This relatively straight and smooth fluid flow path allows the pumped fluid to flow through the nozzle with relatively little head loss, thus allowing lesser force to dispense the fluid and otherwise facilitating precise control over the type of fluid flow to be emitted at the dispensing tip, such as control over drop size, flow velocity, or spray droplet size, spray pattern, etc.

Yet another advantage of the illustrated pump configuration is that the bellows 148 is sealed relative to the variable-stroke volume 113 to thereby prevent any of the medicament or other substance contained within the chamber 55 from collecting in the space between the bellows and the piston or slide. As can be seen, the o-ring or like seal 90 forms a fluid-tight seal between the piston and the slide, thus preventing any fluid from flowing therethrough and into the bellows. Similarly, fluid-tight seals are formed at the interfaces of the cover 62, nozzle 58 and slide 60, including fluid-tight seals at the interfaces of the slide engagement portion 158 of the cover and the slide 60, and at the interface of the annular rib 126 of the cover and at the annular groove 122 of the nozzle 58.

Referring now to FIGS. 9 and 9A, the vial 52 is preferably composed of a suitably rigid and moldable material, such as a rigid polymeric material, e.g., polycarbonate or polyvinyl-chloride. Preferably, this material is selected to be compatible with a wide variety of medicaments, such as that sold under the trademark Lexan of the General Electric Corporation of Pittsfield, Mass. The vial 52 is tubular in configuration and comprises an outer wall 77 that defines the main fluid chamber 55, the annular mounting flange 78 discussed above in connection with FIGS. 2 and 4, and an annular connecting portion 162 formed on an opposite end of the vial relative to the mounting flange 78. The main fluid chamber 55 is dimensioned such that it is large enough to contain a predetermined quantity of a fluid to be dispensed, such as a medicament, along with the flexible bladder 54 (FIG. 2) discussed in more detail below. The mounting flange 78 includes an annular ridge 164 for mounting the vial 52 into sealing engagement with the nozzle cover 62 (FIG. 2) and preventing movement of the cover during use of the dispenser 10. As seen in FIGS. 2 and 3, the mounting portion 146 of the cover 62 is sandwiched between the base 64 of the piston 56 and the rigid vial 52 to form a fluid-tight seal.

As shown in FIG. 9A, the annular connecting portion 162 comprises a tapered end 166 and a peripheral groove 168 spaced inwardly therefrom on an increased diameter portion 170. An annular ridge 172 is provided for engaging the flexible bladder 54 (FIG. 2). As described further below, the increased diameter portion 170 and annular ridge 172 function to allow hermetic sealing of the main fluid chamber 55 after assembly of the vial 52. As also described further below, an annular groove 174 is provided for retention of the vial 52 during filling of the main fluid chamber 55.

Figure 10:
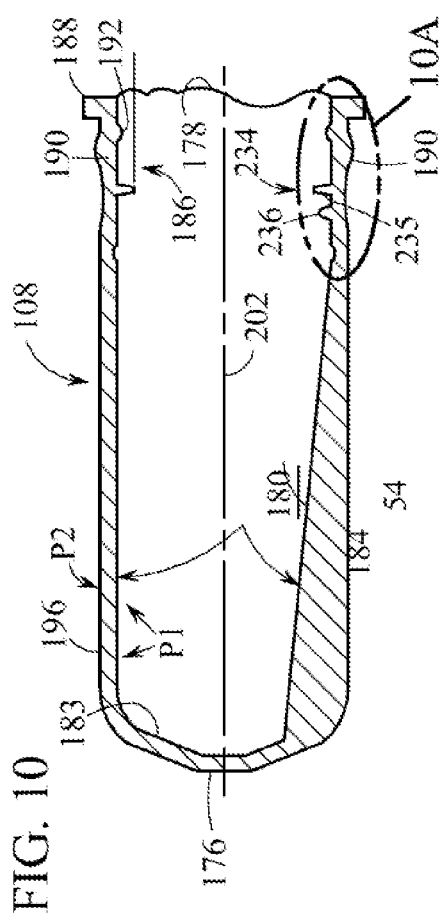
FIG. 10 is a central, cross-sectional view taken along a longitudinal axis of the bladder of the dispenser of FIGS. 2 and 3 showing in this configuration a three-ribbed structure provided to allow the bladder to collapse into a predetermined collapsed condition.

Referring now to FIG. 10, the flexible bladder 54 may be composed of any suitably flexible material, and preferably defines barrier properties to prevent the passage therethrough of vapor, moisture and gas. For ease of manufacture, the material preferably may be molded and is compatible with a wide variety of medicaments or other substances to be contained within the chamber 55, and therefore in a preferred embodiment may be formed of a rubber or synthetic rubber. Alternatively, the flexible bladder 54 may be composed of a thermo-elastic material, such as the styrene-butadiene elastomer sold under the trademark KRATON as discussed above in connection with the pump cover 62. Similarly, materials sold under the trademarks VISKAFLEX owned by the AES Company, ALCRYN or HYTREL owned by the Dupont Company of Wilmington, Del., and SARLINK owned by the DSM Company may be used instead. These materials are only exemplary, however. As may be recognized by those skilled in the pertinent art based on the teachings herein, the flexible bladder may be made of any of numerous other materials that are currently or later become known for performing the function of the flexible bladder as disclosed herein.

In the currently preferred embodiments, the flexible bladder 54 is made of a resilient material as described above and is molded in the expanded condition. Accordingly, when collapsed in the manner described further below, the resilient bladder tends to force itself outwardly and, in turn, increase the pressure of the medicament or other fluid in the main fluid chamber 55 in comparison to the pressure in the interior of the bladder. A significant advantage of this pressure differential is that it facilitates in preventing the ingress of air, other gases or vapors located within the interior chamber of the bladder through the bladder or otherwise into the main fluid chamber. As a result, the dispensers of the present disclosure are particularly well suited for containing multiple dose, non-preserved medicaments or other substances, and in maintaining such substances in a sterile, airless condition, throughout substantial periods of storage, shelf life and/or use of the dispensers. This advantageous feature also facilitates in preventing any changes in the ambient conditions of the dispenser from affecting the airless condition of the main fluid chamber 55, and otherwise prevents the ingress of air, other gases or vapors into the main fluid chamber.

Figure 10B:
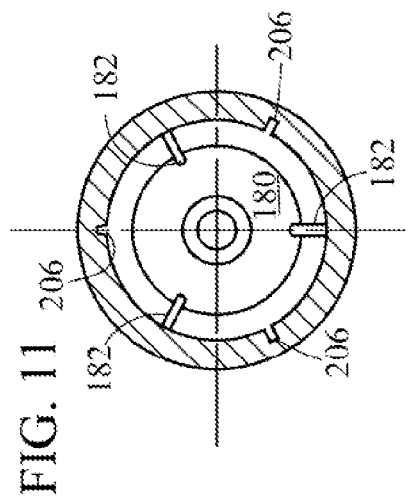
FIG. 10B is a highly enlarged view of a portion of the bladder of FIG. 10.

The flexible bladder 54 preferably also provides a barrier to the passage of gas, such as air, through the flexible bladder, and thus may be composed of a single layer of material that has a substantially reduced permeability to air. In one embodiment, the bladder 54 is composed of a multi-layered material. For example, as illustrated in FIG. 10B, a bladder wall 175 may comprise a first flexible layer 177 of an elastomer that is relatively porous to air, and a barrier layer 179, such as a metallized MYLAR, e.g., an aluminum and polyester composition, sold by the Dupont Corporation of Wilmington, Del., that is relatively impervious to air. The barrier layer 179 may be disposed between a polyethylene upper layer 181 and lower layer 183 to facilitate adhesion of the barrier layer to the bladder wall 175 while maintaining flexibility. Alternatively, the barrier layer 179 may be composed of polyvinylidene chloride sold under the mark SARAN owned by the Dow Chemical Company of Midland, Mich. It will be appreciated that the barrier layer 179 is preferably dimensioned to cover as much of the bladder wall 175 as permitted in order to reduce the passage of air therethrough without interfering with the various functions of the flexible bladder as more fully described below. The barrier layer 179 is also preferably disposed on the interior of the bladder wall 175. Optionally, the barrier material may be a butyl rubber-based material, such as that used for the manufacture of syringe stoppers, or used in the tire industry. As may be recognized by those skilled in the pertinent art based on the teachings herein, the flexible bladder and barrier materials disclosed herein are only exemplary, and any of numerous other materials that are currently known, or later become known for performing the functions disclosed herein, may be equally employed.

Referring now again to FIG. 10, the flexible bladder 54 is tubular in configuration and comprises a closed end 176 and an open end 178 that fluidly communicates with a cavity 180. The bladder 54 defines an external diameter dimensioned to fit within the vial 52 (FIG. 2) when in the expanded condition as shown in FIG. 10. As shown in FIGS. 2 and 3, the outer surface of the bladder 54 preferably defines a shape or morphology substantially the same as that of the interior surface of the rigid vial 52 so that upon expanding the flexible bladder, the flexible bladder conforms to and contacts the rigid vial throughout the interface of these two components to thereby eliminate any ullage or dead space between the components, and force all of the medicament or other substance within the chamber 55 into the variable stroke volume 113 of the pump 50 for dispensing therefrom. In addition, the outer diameter (or width) of the flexible bladder when fully expanded is preferably slightly greater than the inner diameter (or corresponding width) of the rigid vial, so that the expanded bladder may exert a resilient force against the vial to maintain at least a slight pressure differential between the chamber 55 on one side of the bladder and the interior of the bladder and thereby prevent the ingress of air, other gases or vapors through the bladder and into the main fluid chamber, as described above.

Figure 11:
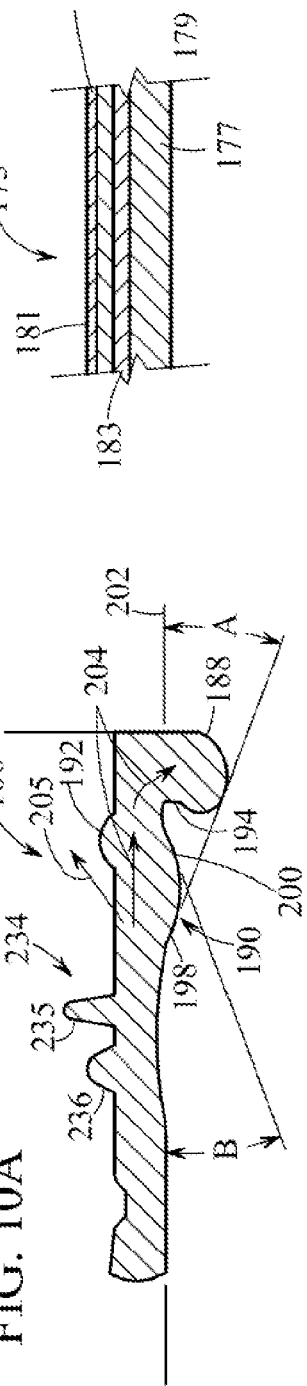
FIG. 11 is a cross-sectional view taken along a transverse axis of the bladder of FIG. 10.

As shown in FIG. 10 and FIG. 11, longitudinally extending stiffeners or rib portions 182 are disposed along the inside surface 184 and function to provide a supporting structure about which the bladder 54 may collapse as will be described in more detail below in conjunction with FIG. 12. To achieve this, the rib portions 182 extend axially along the interior surface 184 and are approximately equally spaced about the circumference of the interior surface. It will be recognized that other configurations of the rib portions 182 and/or locations at which the rib portions may be employed are contemplated. For example, the rib portions 182 also may extend along the inside surface 183 of the closed end 176 of the flexible bladder 54.

Figure 10A:
FIG. 10A is an enlarged view of a portion of the bladder of FIG. 10.

As illustrated in FIGS. 10 and 10A, the flexible bladder 54 includes a mounting portion 186 that comprises an annular flange 188 formed at the rear end of the bladder, an outer annular lobe 190 spaced axially inwardly relative to the flange 188, and an inner annular lobe 192 spaced between the outer annular lobe 190 and the flange 188. As shown in FIG. 10A, the annular flange 188 defines on its underside an annular, V-shaped indent 194 for sealing engagement with the annular ridge 172 of the vial 52 (FIG. 9A). In addition, the annular flange 188 is over-sized so that during initial assembly with the vial 52, as will be discussed in more detail below, the peripheral surface of the annular flange may engage the corresponding annular groove 168 of the vial 52 (FIG. 9A).

During storage and/or shelf life of the dispenser 10, the material of the flexible bladder 54 may flow or move in order to equalize the tensile and compressive forces that it is subject to. Creep, as used herein, refers to a change in property of the material wherein there is a loss in resilience and memory of the material. In particular, after undergoing creep the elastic material may permanently deform and lose at least some of its original elasticity. Accordingly, after assembly and during filling of the dispenser 10, the cavity 180 of the flexible bladder 54 may be subject to low pressure which causes collapse and elastic deformation thereof which is maintained by the pressure of fluid filled in the main fluid chamber 55 (FIG. 2). Thereafter, the filled dispenser may be maintained in storage and/or on a store or other shelf for at least two or more months prior to use, during which the material of the bladder may undergo creep causing at least some deformation thereof. To properly manage the movement of the material during creep of the flexible bladder 54, and as shown best in FIG. 10A, the bladder is provided with the outer annular sealing lobe 190 and the inner annular sealing lobe 192 spaced axially between the outer sealing lobe and the flange 188 so that, when creep resulting from compression of the elastomeric or rubber-like material occurs, the intra material pressure is balanced in between the two lobes 190,192 and a persistent, fluid-tight seal is provided. This mechanical seal can then be maintained due at least in part to the material reservoir formed by the inner lobe 192 in which creeping material in the outer lobe 190 offsets that of the inner lobe.

Figure 14:
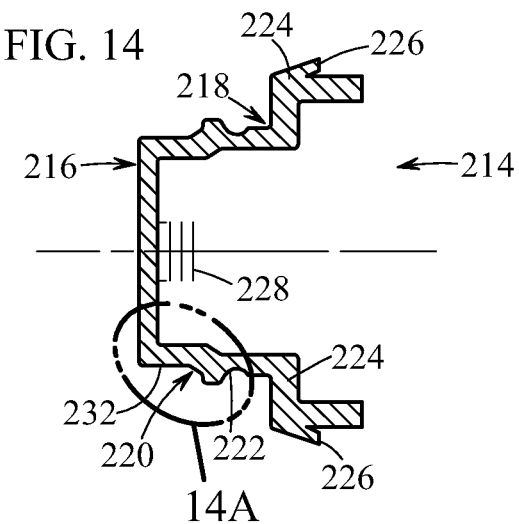
FIG. 14 is a sectional view of the rear plug taken along line 14-14 of FIG. 13.

As shown in FIG. 10A, the outer annular lobe 190 comprises a first angular portion 198 located on one side of the lobe 192, and a second angular portion 200 disposed on the opposite side of the lobe. The first angular portion 198 defines a first acute angle "A" with respect to a center axis 202 that may be within the range of approximately 0° to approximately 30°, and more preferably within the range of approximately 0° to approximately 10°. The second angular portion 200 defines a second acute angle "B" relative to the axis 202 that may be within the range of approximately 0° to approximately 15°, and more preferably within the range of approximately 0° to approximately 5°. In order to ensure that during creeping of the material of the flexible bladder 54 the material moves approximately in the directions of the arrow 204 and arrow 205, the first angle A is larger than the second angle B and the flexible bladder is axially fixed by the inner annular sealing lobe 192 received within the corresponding annular groove 222 of the rear plug (FIG. 14). As shown in FIGS. 2 and 3, when the flexible bladder 54 is fully received within the rigid vial 52, the outer annular lobe 190 is pressed against the smooth interior wall of the vial, the inner annular lobe 192 is received within the corresponding annular groove 222 of the rear plug (FIG. 14), and the annular flange 188 is sandwiched between the rear plug and the annular ridge 172 of the rigid vial. Thus, the inner annular sealing lobe 192 functions as a material reservoir for the outer annular sealing lobe 190, and as indicated by the arrows 204 and 205, the axially-offset lobes cause the material to flow generally from the outer lobe 190 toward the inner lobe 192, and from both lobes generally toward the annular flange 188. As a result, the material flow is persistently directed toward the inner sealing lobe 192 and/or annular flange 188 to thereby maintain a fluid-tight seal between the flexible bladder, rigid vial and rear plug, regardless of the degree of creep of the bladder material. As can be seen, the shape and relative position of the outer annular lobe 190 as described above facilitates in directing the forces within the bladder and thus the material in the directions of the arrows 204 and 205 to thereby maintain the fluid-tight seal throughout the storage, shelf-life and usage of the dispenser 10.

As shown in FIG. 11, the flexible bladder 54 preferably also comprises at least one surface discontinuity 206 that facilitates and controls the collapse of the bladder from a tubular configuration to a predetermined collapsed configuration to thereby substantially eliminate the volume of the cavity 180 defined by the interior of the bladder. In the illustrated embodiment, the flexible bladder comprises three surface discontinuities 206 located on the interior surface 184 of the bladder and approximately equally spaced relative to each other. As can be seen, the discontinuities 206 are each approximately equally spaced between adjacent elongated ribs 182. The discontinuities 206 are illustrated in the configuration of a crevice or crack terminating in a generally flat center portion (not numbered) in cross section as shown. As can be seen, the surface discontinuities 206 cause the bladder to collapse or fold onto itself about each elongated rib 182 to thereby form in the collapsed condition three folded sections or legs spaced about 120° relative to each other. As may be recognized by those skilled in the pertinent art based on the teachings herein, and illustrated by the additional embodiments below, any of numerous other structures or configurations may be equally employed to collapse the bladder into a predetermined shape, such as the predetermined collapsed shape formed by discontinuities and elongated ribs described above.

Figure 12:
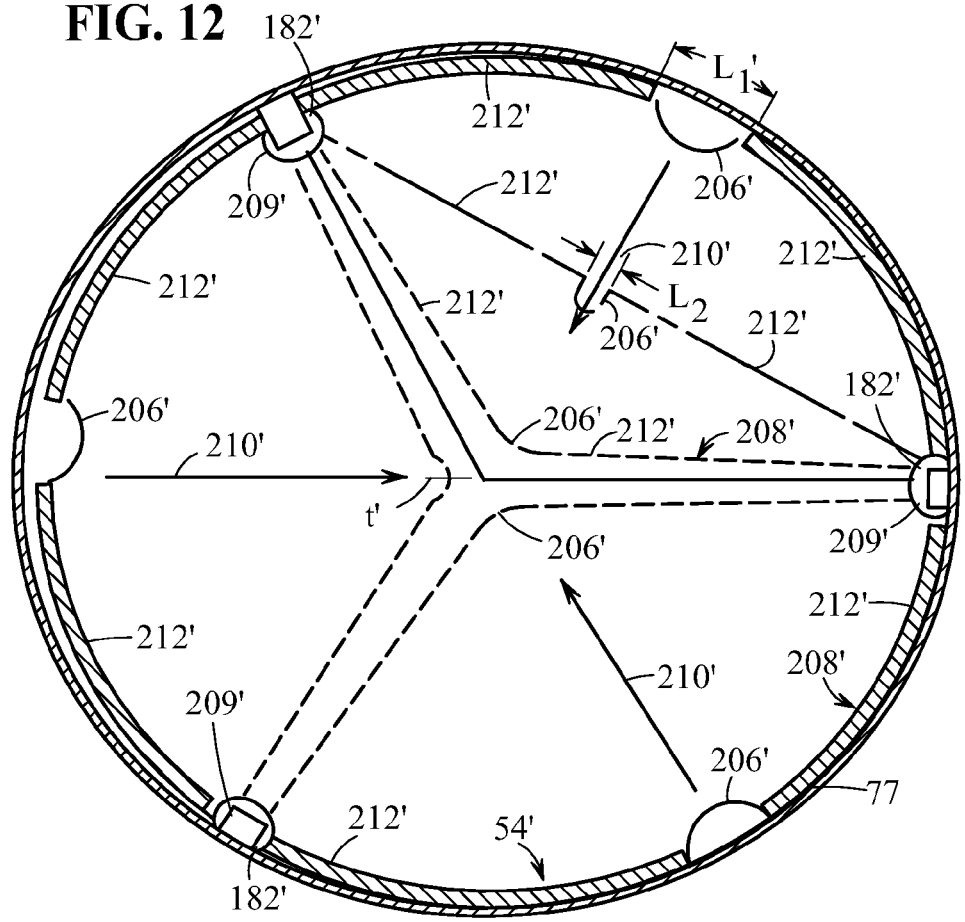
FIG. 12 is a schematical view showing, in cross section, another embodiment of the bladder of the dispenser of FIGS. 2 and 3 disposed within the rigid vial and including elongated discontinuities or elongation buffers disposed in an outer wall of the bladder to facilitate the collapse of the arcs that pass through the chords of the respective arcs.

Referring now to FIG. 12, a cross section of an outer wall 208' of a flexible bladder 54' is illustrated in schematic. The flexible bladder 54' is capable of collapsing in the direction of arrows 210' from an expanded position, shown in solid lines adjacent to the outer wall 77 of the vial 52 (FIG. 9) to a collapsed position shown in broken lines. The flexible bladder 54' is functionally similar to the flexible bladder 54 and thus like elements are labeled with like reference numerals followed by the prime (') symbol. However, it will be recognized that some differences in structure exist between the flexible bladder 54 and the flexible bladder 54'. For example, discontinuities 206' are illustrated as being inverted with respect to the discontinuities 206 and generally cover the entire cross-sectional thickness (t') of the wall 208'. While the discontinuities 206' are illustrated as generally arcuate in configuration, it will be appreciated that other configurations, such as that of discontinuities 206, which also perform the function described below may be employed instead. Also, it will be appreciated that the rib portions 182' define mounting slots 209' for receiving therein correspondingly-shaped portions (not shown) of the vial 52.

It will be understood that both the discontinuities 206 and 206' function to allow for a reduction in length of the portions of the wall 208' necessary to collapse the flexible bladders 54 and 54'. While this function is being described in connection with the embodiment of FIG. 12, this description is equally applicable to the embodiment of FIG. 11. As shown in FIG. 12, the wall 208' comprises a plurality of wall portions 212' extending between each discontinuity 206' and adjacent rib portion 182', and as shown in solid lines each wall portion 212' forms an arc when the bladder 54' is expanded. It will be recognized that during collapsing of the bladder 54' in the directions of the arrows 210', the wall portions 212' become approximately linear and form a chord as shown in the dashed and dotted lines, and then inversely arcuate as illustrated in the dashed lines. Accordingly, as illustrated, a length L1 of the discontinuities 206' shown in solid lines shortens to a length L2 shown in dotted and dashed lines to thereby allow free movement of the arcs 212' in the direction of the arrows 210'. Once the flexible bladder 54' has collapsed, the bladder may expand and the wall portions 212' may freely move in a direction opposite that of the arrows 210'.

Figure 13:
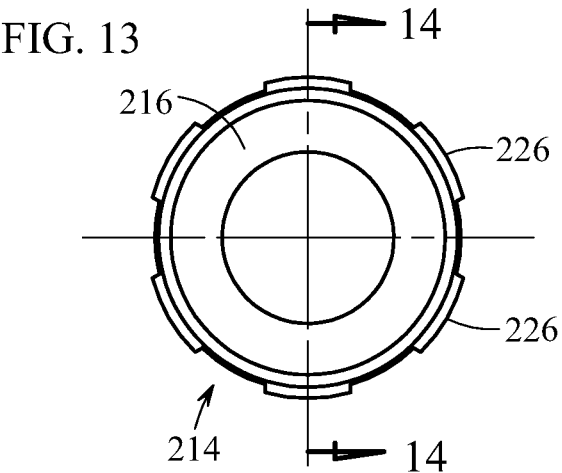
FIG. 13 is a top plan view of the rear plug employed to close the rear end of the inner bladder by forming a sandwich-type structure between the rigid vial and rear plug to hermetically seal the dispenser of FIGS. 2 and 3.
Figure 14A:
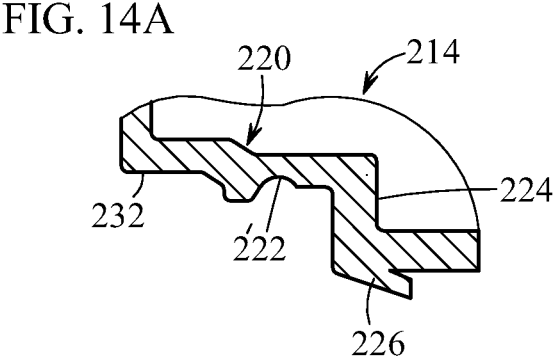
FIG. 14A is an enlarged portion of the rear plug of FIG. 14 showing further detail of an annular side wall of the plug.

As illustrated in FIGS. 13 and 14, the flexible bladder comprises a rear plug 214 configured to mate with the open end 178 of the flexible bladder 54 (FIG. 2) and to seal the flexible bladder 54 disposed between the rear plug and the rigid vial 52. The rear plug 214 may be composed of any suitably strong, moldable and durable material, such as a polymeric material, e.g., polyethylene, and is preferably composed of Lexan™ or a like polycarbonate for its stress-resistant properties. The rear plug 214 comprises an end wall 216 and a side wall 218 that, as seen best in FIG. 14A, preferably includes a tapered portion 220 defining a gradually increasing diameter in the direction of the rear end of the plug, an annular groove 222 spaced rearwardly of the tapered portion 220, a stepped portion 224, a plurality of outwardly-protruding protective tabs 226 (or bumps for ease of manufacturing) angularly spaced relative to each other about the axis of the plug, and an aperture 228 extending through the side wall for allowing fluid communication between the interior chamber 180 of the bladder and the ambient atmosphere. The tapered portion 220, because of the increasing diameter thereof, provides for ease of assembly of the plug 214 to the flexible bladder 54 (FIG. 2) and defines an annular space 230 (FIG. 2) located between the plug and the adjacent surface of the flexible bladder. As described above and shown in FIGS. 2 and 3, the annular groove 222 is configured to receive the inner annular lobe 192 (FIG. 10) and the stepped portion 224 sandwiches the annular flange 188 of the flexible bladder 54 against the annular ridge 172 of the rigid vial. As best seen in FIGS. 13 and 14, the safety sealing tabs 226 project upwardly and outwardly from the stepped portion 224 and are angularly spaced relative to each other about the axis of the plug. The sealing tabs 226 are provided for locking the plug 214 to the vial 52 (FIG. 2) and are configured to snap-fit within the annular groove 168 of the vial (FIG. 9) upon being pressed against the annular flange 188 of the bladder to thereby maintain an airtight seal. In addition, because the sealing tabs 226 are tapered outwardly as shown typically in FIG. 14A, the tabs easily snap into the annular groove 168 of the vial; however, the tabs cannot be moved out of the groove in the opposite direction and thereby form a tamper-proof seal. The aperture 228 provides for fluid communication between the annular space 230, chamber 180 (FIG. 2) and ambient atmosphere, and is illustrated as being generally rectangular in configuration. However, it will be understood that other configurations, such as circular or other shapes, may be employed, providing that a sufficient volume of air may pass therethrough to fill the interior chamber 180 of the flexible bladder 54.

Returning to FIGS. 10 and 10A, the flexible bladder 54 also preferably comprises a two-way valve 234 axially spaced below the sealing lobes 190 and 192 for controlling the flow of air between the interior chamber 180 of the bladder and ambient atmosphere. The valve 234 comprises an annular operator 235 projecting inwardly from the interior wall of the bladder and having a generally ridge-like configuration in cross section. As shown in FIGS. 2 and 3, the end portion of the annular operator 235 engages the annular surface 232 formed at the base of the rear plug 214, and is disposed between the annular space 230 and the interior chamber 180 of the bladder. The flexible bladder 54 further defines a plurality of support protuberances 236 that are axially spaced adjacent to the annular operator 235 and angularly spaced relative to each other about the axis 202.

The end surface of each protuberance 236 is spaced inwardly relative to the end of the annular operator 235 to thereby allow the operator 235 to engage and seal the interface between the operator and rear plug, while simultaneously ensuring sufficient radial spacing between the rear plug and flexible bladder for allowing movement of the operator 235 in either direction. Thus, as can be seen, the operator 235 and annular wall 232 of the rear plug form a two-way valve allowing fluid to flow therethrough when the differential pressure across the valve is sufficient to axially flex the operator. It will be understood that the rigidity of the operator is set to allow fluid to pass therethrough when the pressure differential exceeds a predetermined threshold pressure. Thus, a significant advantage of the valve 234 is that it maintains a relatively stable micro-atmosphere within the inner chamber 180 of the flexible bladder 54 and prevents a regular exchange of air, other gases or vapors between the micro-atmosphere within the bladder and the ambient atmosphere. For example, the valve 234 allows air to be drawn into the chamber 180 upon dispensing the medicament or other substance from the main fluid chamber 55 to thereby allow the bladder to expand and fill the space of the dispensed medicament. However, the valve 234 otherwise prevents air or vapors from flowing freely between the micro-atmosphere and the ambient atmosphere. Thus, the micro-atmosphere within the chamber 180 may define different pressure and/or humidity levels in comparison to the ambient atmosphere. A significant advantage of this feature is that it insulates the micro-atmosphere from fluctuations in the pressure and/or humidity levels of the ambient atmosphere, thereby maintaining relatively stable pressure and humidity levels within the micro-atmosphere and thus preventing the ingress of air or vapors through the bladder wall and into the main fluid chamber.

In FIGS. 15A-15C, the dispenser 10 is illustrated in the full, half-full and empty conditions, respectively. In FIG. 15A, the main fluid chamber 55 is filled with, e.g., a medicament (not shown) that the pump assembly 50 may pump outwardly of the nozzle 58. Accordingly, the bladder 54 is illustrated in a collapsed state. In FIG. 15B, the flexible bladder 54 is shown in an expanded condition whereby the bladder has expanded to displace the volume of medicament dispensed from the main fluid chamber 55. To achieve this result, air has passed in the direction of arrow 240, through the valve 234 and into the interior chamber 180 of the flexible bladder. In FIG. 15C, the dispenser 10 is illustrated in an empty condition. As can be seen, the bladder 54 is fully expanded against wall 77 of the rigid vial and substantially conforms to the morphology of the rigid vial to thereby eliminate any ullage or dead space and force all medicament or other substances therein into the pump 50.

Figure 16A:
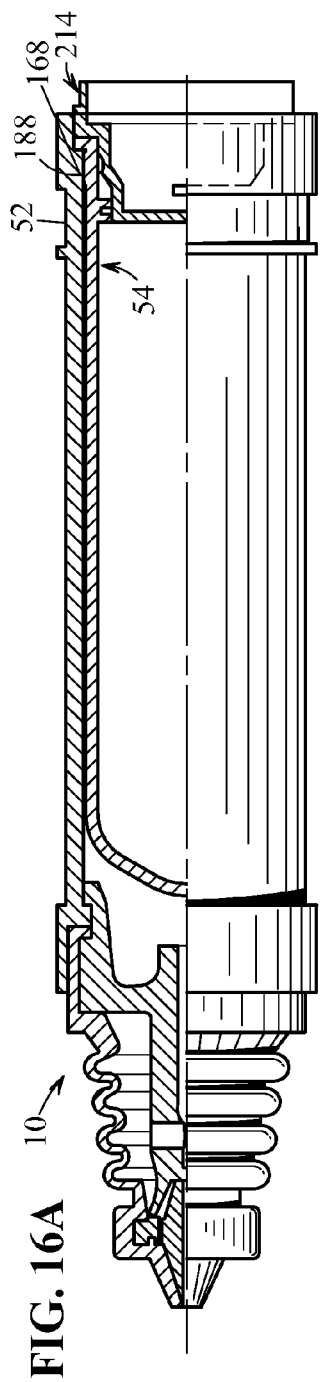
FIGS. 16A-C are sequential side elevational views, partly in section, showing the steps of assembling the bladder to the vial during sterilization and filling of the dispenser of FIGS. 2 and 3.
Figure 16B:
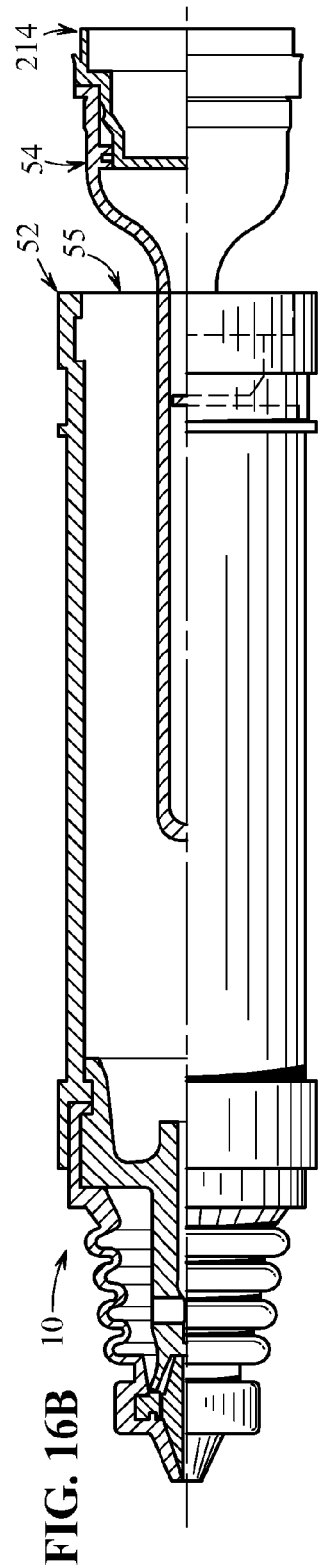
Figure 16C:
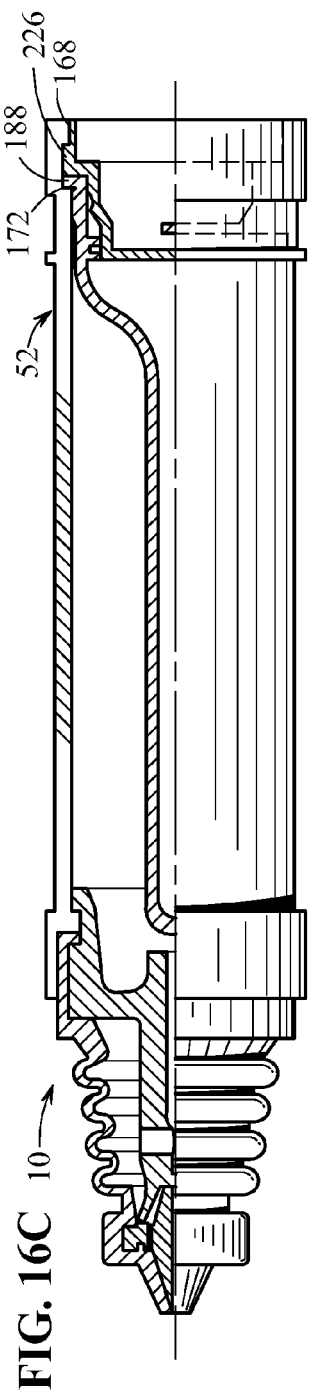

Referring now to FIGS. 16A-16C, initial assembly of the dispenser 10 for purposes of sterilization, e.g., by irradiation of energy rays, is illustrated in FIG. 16A. In particular, the rear plug 214 is fitted to the flexible bladder 54, and the plug and flexible bladder are partially inserted into the vial 52. Turning now also to FIGS. 9A and 10, the flange 188 of the flexible bladder 54, when in the partially inserted position, is disposed within the annular groove 168 of the vial 52 to thereby form an air-tight, but not a tamper-proof seal between the bladder and vial. In this state, the dispenser 10 may be sterilized and/or transported in a sealed condition prior to filling the dispenser with a medicament or other substance to be contained therein.

The filling of the dispenser 10 is illustrated schematically in FIG. 16B, wherein the flexible bladder 54 and plug 214 are separated from the vial 52 so that the main fluid chamber 55 may be accessed for filling. As can be seen, the annular flange 188 of the bladder may be pulled rearwardly and removed from the annular groove 168 of the vial to thereby open the vial and access the main fluid chamber 55. Preferably, this operation is carried out by transporting the sterilized dispensers through a sterile transfer port, and filling the dispensers within a sterile filling machine of the types disclosed in commonly-assigned U.S. Pat. Nos. 5,641, 004 and 5,816,772, which are hereby expressly incorporated by reference as part of the present disclosure. During filling, a vacuum may be drawn on the inner chamber 180 of the bladder to collapse the bladder, and the medicament or other substance to be contained therein may be introduced into the main fluid chamber 55.

As shown in FIG. 16C, upon filling the main fluid chamber 55 with the medicament or other substance to be contained therein, the flexible bladder and rear plug assembly are moved into the rigid vial such that the flexible flange 188 of the bladder is moved into engagement with the annular ridge 172, best seen in FIG. 9A, and the rear plug is pressed inwardly until the sealing tabs 226 are snapped into place within the annular groove 168 of the vial to thereby form the airtight and tamper-proof seal. The dispenser 10 may then be installed within the ocular treatment apparatus 8 described above or other suitable apparatus for dispensing medicaments or other fluids, such as nasal inhalers.

In FIGS. 17 through 20, another embodiment of the dispenser of the present disclosure is indicated generally by the reference numeral 310. The dispenser 310 is substantially similar to the dispenser 10 described above, and therefore like reference numerals preceded by the numeral "3", or preceded by the numeral "4" instead of the numeral "1", or preceded by the numeral "5" instead of the numeral "2", respectively, are used to indicate like elements. The primary differences of the dispenser 310 in comparison to the dispenser 10 are that (i) the rigid vial 352 and piston 356 are formed as integral components; (ii) the nozzle 358 and slide 360 are formed as integral components; (iii) the flexible bladder 354 defines a smooth cylindrical configuration without any discontinuities or ribs formed thereon; and (iv) the rear plug 514 includes a plurality of inwardly projecting legs 538 for controlling the collapse of the flexible bladder into a predetermined collapsed shape.

Figure 21:
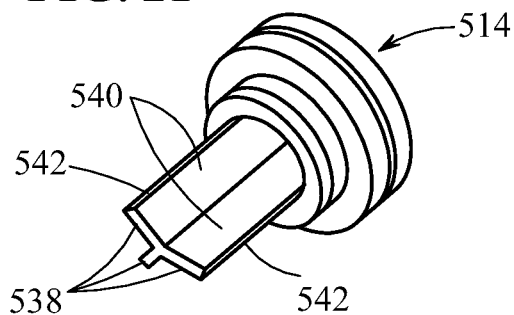
FIG. 21 is a perspective view of the rear plug of the dispenser of FIG. 17.
Figure 22:
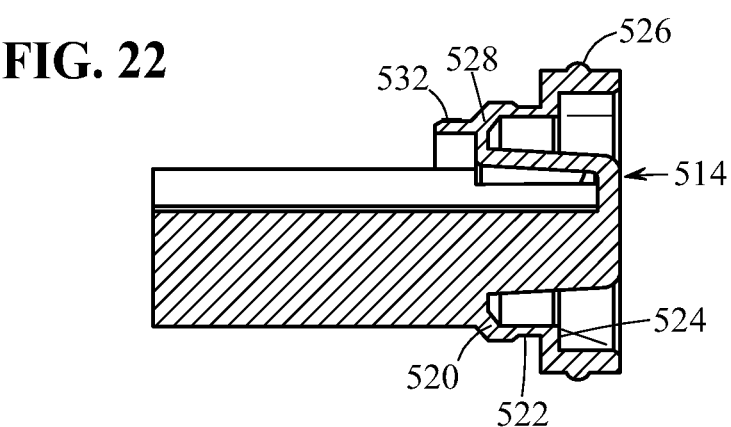
FIG. 22 is cross-sectional view of the rear plug of FIG. 21.
Figure 23:
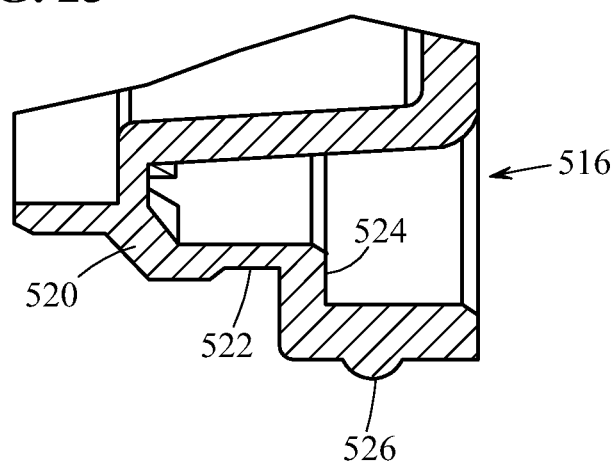
FIG. 23 is a partial, enlarged cross-sectional view of the rear plug of FIG. 21.
Figure 24:
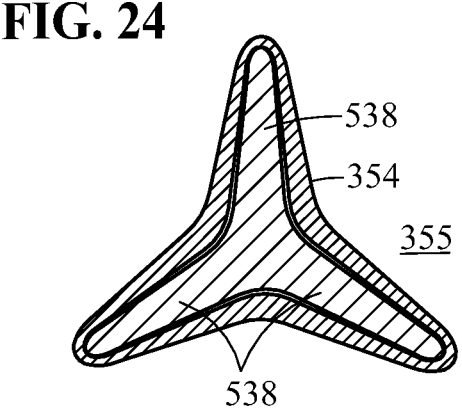
FIG. 24 is a partial, cross-sectional view of the axially-extending and radially-projecting legs of the rear plug of FIG. 21 illustrating the flexible bladder conformably engaging the legs in the predetermined collapsed condition.
Figure 25:
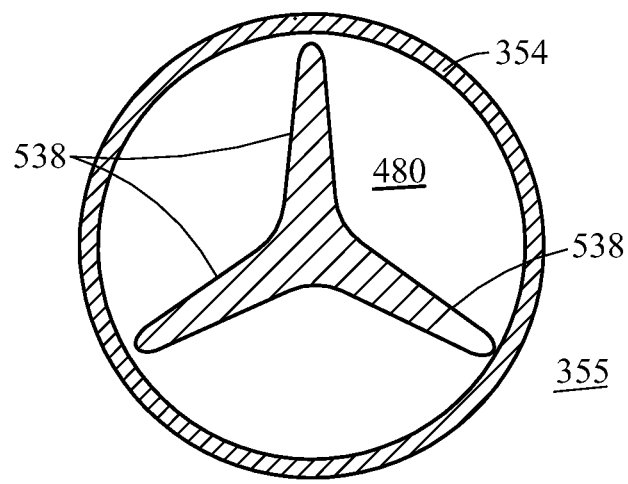
FIG. 25 is a partial, cross-sectional view of the legs of the rear plug and bladder illustrating the bladder in the expanded condition.

As shown in FIGS. 21-23, the rear plug 514 defines a plurality of inwardly projecting, axially-elongated legs 538 defining a framework within the interior chamber 480 of the flexible bladder 354 for controlling the collapse of the bladder into a predetermined collapsed shape. As shown in FIG. 21, the currently preferred embodiment includes three legs 538 angularly spaced approximately 120° relative to each other about the axis of the rear plug. Each leg lies in a respective plane intersecting the axis of the rear plug and defines approximately planar side surfaces 540 extending radially between the axis of the plug and the inner wall of the rigid vial. As shown in FIGS. 19 and 20, the radial edge 542 of each leg is radially spaced inwardly relative to the inner wall of the rigid vial to thereby allow movement of the flexible bladder between the radial edges of the legs and the vial. As also shown in FIGS. 19 and 20, the legs 538 extend axially into the interior chamber 480 of the flexible bladder a distance sufficient to allow the legs to control the collapse of the bladder into the predetermined collapsed condition. In the illustrated embodiment, each leg 538 extends along at least about one-half the axial extent of the bladder. As shown in FIG. 24, in the predetermined collapsed condition, the flexible bladder 354 conformably engages the outer surfaces of the legs 538 to thereby allow the main fluid chamber 355 to be filled with a medicament or other substance. Then, as shown in FIG. 25, upon dispensing all of the medicament or other substance from the main fluid chamber 355, the resilient nature of the flexible bladder 354 causes the bladder to expand outwardly away from the legs 538. As shown typically in FIGS. 19 and 20, when fully expanded, the flexible bladder 354 conformably engages the inner wall of the rigid vial to thereby eliminate any ullage or dead space and allow all of the medicament or other substance contained with the main fluid chamber 355 to be dispensed therefrom.

As described above, the flexible bladder 538 is preferably made of a relatively low permeability elastomer, such as a vulcanized butyl rubber, or other rubbers. Such rubbers have demonstrated proven stability and/or compatibility with a wide variety of medicaments, such as pharmaceutical preparations and vaccines, and other substances, and therefore are currently preferred for such applications. In the currently preferred embodiment, the flexible bladder 354 is molded in its expanded condition, and when collapsed, the resilient nature of the bladder tends to force the bladder outwardly toward its expanded condition. The resilient forces within the bladder apply a pressure against the fluid within the main fluid chamber 355, and therefore create a higher pressure in the main fluid chamber 355 in comparison to that of the interior chamber 480 of the bladder. As a result, the pressure differential prevents the ingress of air or other gases or vapors through either the flexible bladder or rigid vial, or otherwise into the main fluid chamber. Thus, the material and/or configuration of the bladder are preferably selected to maintain a pressure differential sufficient to prevent the ingress of air or other gases or vapors into the main fluid chamber under a variety of atmospheric conditions. As described above, the preferred rubber materials disclosed herein for constructing the flexible bladder are exemplary, and numerous other materials that are currently, or later become known for performing the function of the flexible bladder may be equally employed.

Figure 26:
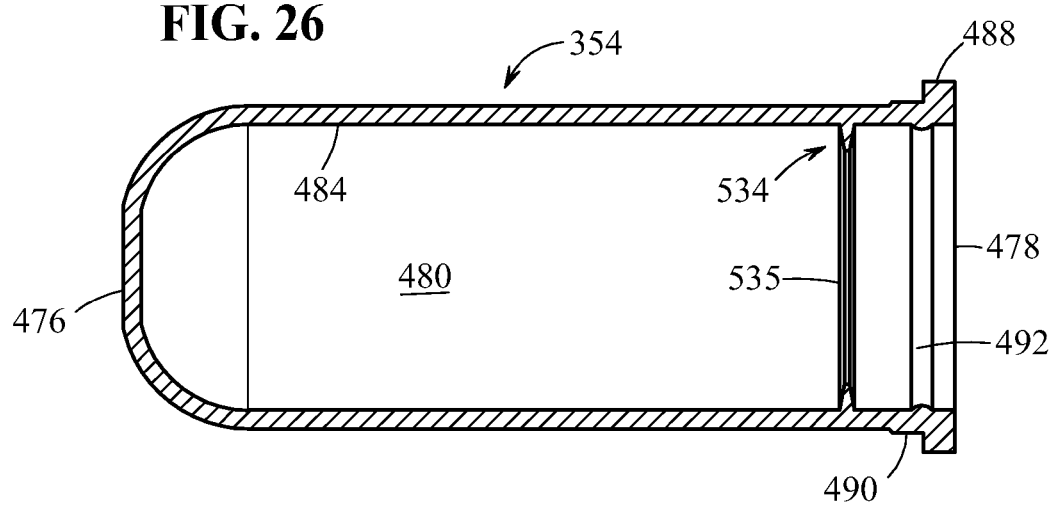
FIG. 26 is a cross-sectional view of the flexible bladder of the dispenser of FIG. 17.
Figure 27:
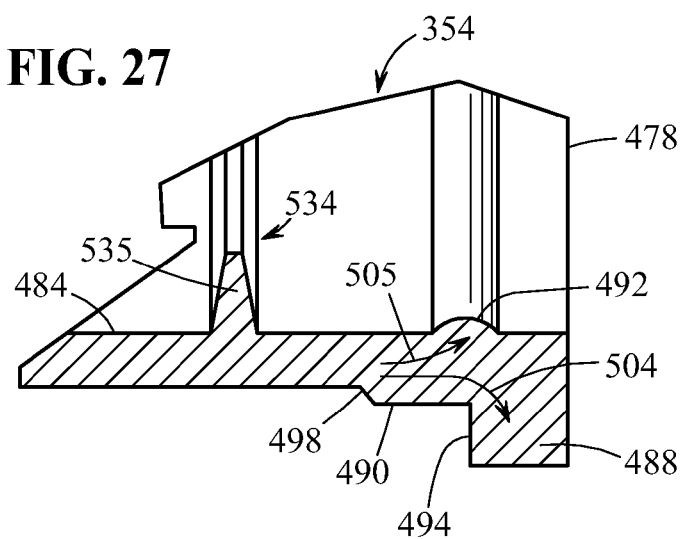
FIG. 27 is a partial, enlarged cross-sectional view of a portion of the flexible bladder of FIG. 26.

As shown in FIGS. 26 and 27, the spaced protuberances 236 described above in connection with the flexible bladder 54 of FIG. 10A may be eliminated depending upon the material of construction and/or other structural features of the flexible bladder 354. In addition, the outer annular lobe may take a shape different than that illustrated above in connection with the bladder of FIG. 10A. As shown in FIG. 27, the outer annular lobe 490 is defined by an annular raised or thickened portion, and a tapered surface 498 extending radially inwardly between the lobe or annular raised portion 490 and the outer peripheral surface of the flexible bladder 354. As shown in FIGS. 19 and 20, the annular raised portion 490 is squeezed against the inner surface of the rigid vial 352 which, in combination with the axially offset, inner annular lobe 492 being fixedly received within the annular groove 522 of the rear end cap (FIG. 23), cause the material of the flexible bladder to creep and/or otherwise flow in the directions of the arrows 504 and 505 in FIG. 27 to thereby persistently maintain an airtight seal between the flexible bladder, rear plug and rigid vial. Thus, the end seal of the flexible bladder is both radially compressed at the axially offset lobes between the rear plug and rigid vial, and is axially compressed at the flange between the rear plug and rigid vial.

Figure 30:
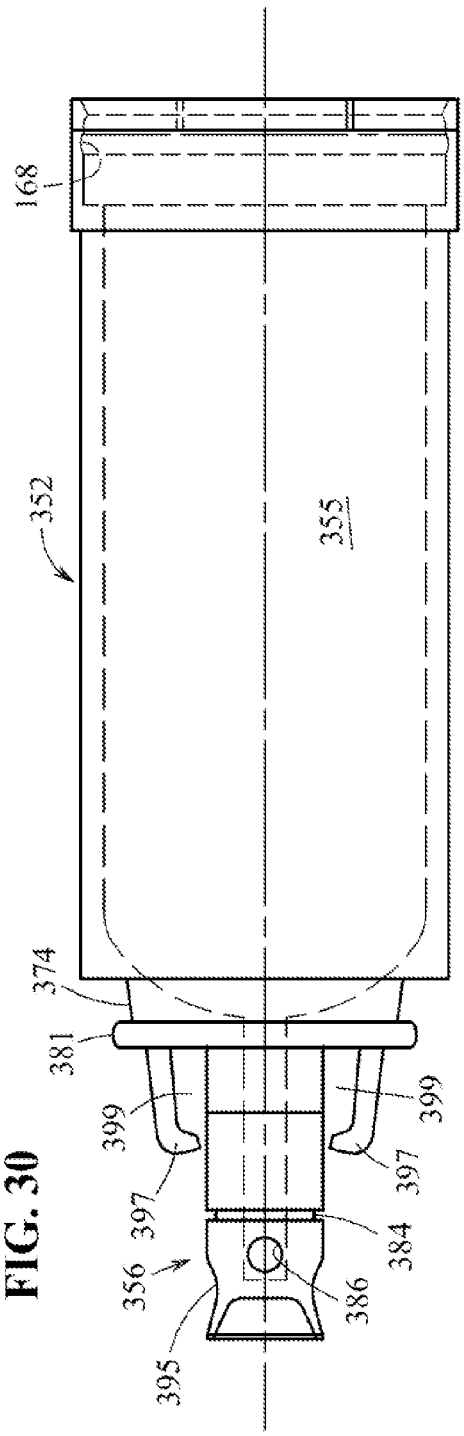
FIG. 30 is a side elevational view of the integral piston and rigid vial of the dispenser of FIG. 17.

As shown typically in FIG. 22, the rear plug 514 defines three apertures 528 approximately equally spaced relative to each other about the axis of the plug. In addition, rather than defining the sealing tabs 226 described above in connection with FIG. 14, the rear plug 514 defines an annular lobe 526 projecting outwardly from the peripheral surface of the rear plug and dimensioned to be snapped into the annular groove 168 of the rigid vial (FIG. 30). The dispenser 310 may be sterilized, temporarily closed, re-opened, and filled in the same manner as described above in connection with FIGS. 16A through 16C.

Figure 28:
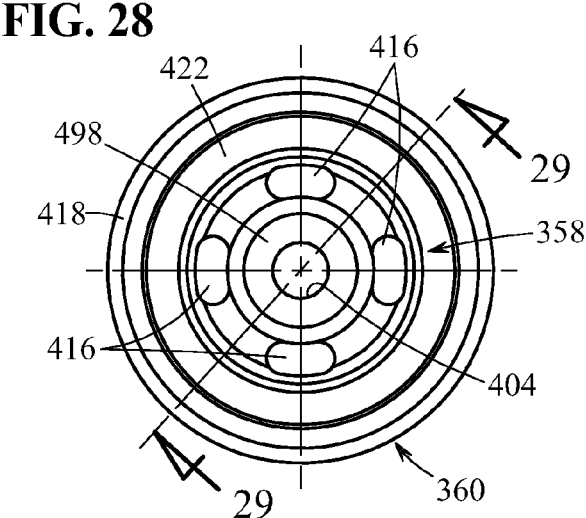
FIG. 28 is a front elevational view of the integral nozzle and slide of the dispenser of FIG. 17.
Figure 29:
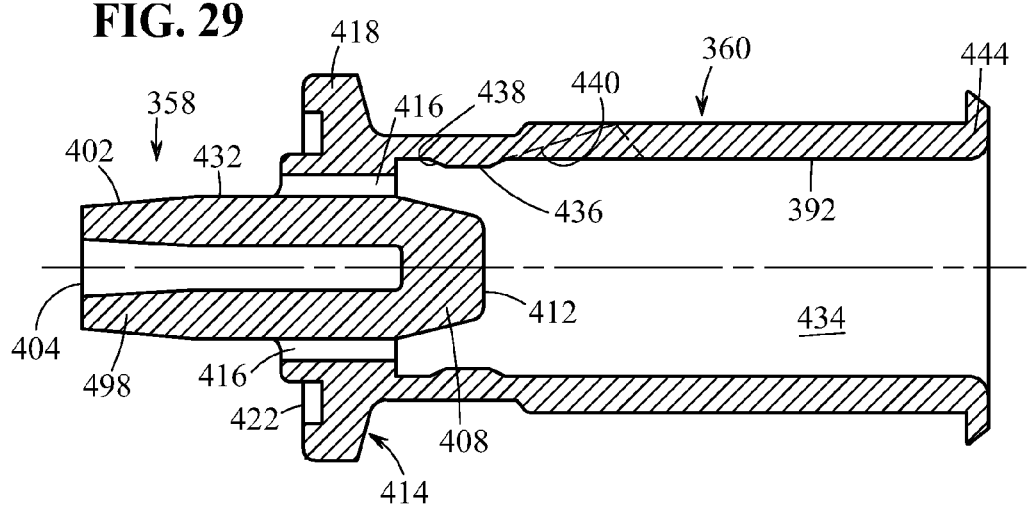
FIG. 29 is a cross-sectional view of the integral nozzle and slide taken along line 29-29 of FIG. 28.

As shown in FIGS. 28 and 29, the nozzle 358 and slide 360 are formed integral with each other. One advantage of this construction over the separate nozzle and slide described above in connection with the previous embodiment, is that the integral construction is typically less costly to manufacture and assemble, and furthermore, reduces the number of seals between components and thereby enhances the overall reliability of the dispenser.

Figure 31:
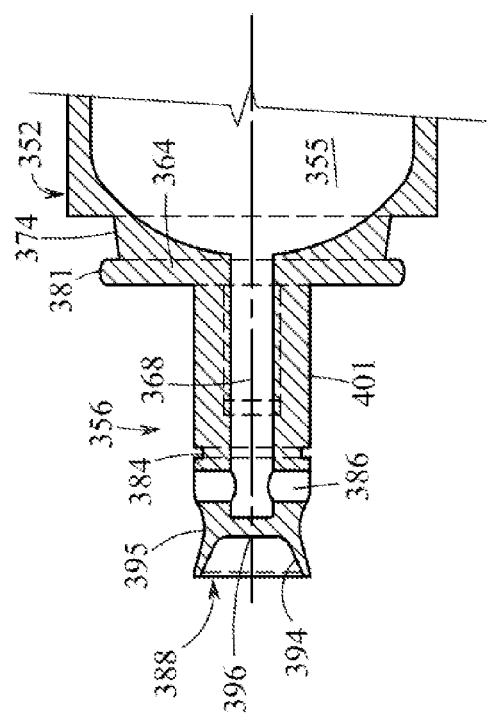
FIG. 31 is a partial, cross-sectional view of the integral piston and rigid vial of FIG. 30.

As shown in FIGS. 30 and 31, the piston 356 and rigid vial 352 are also formed integral with each other. As with the integral nozzle and slide described above, one advantage of this construction over the separate piston and slide described above in connection with the previous embodiment, is that the integral construction is typically less costly to manufacture and assemble, and furthermore, reduces the number of seals between components and thereby enhances the overall reliability of the dispenser. In the currently preferred embodiment, the integral nozzle 358 and slide 360 is made of a relatively soft material, and the integral piston 356 and vial 352 is made of a relatively hard material. In the operation of the dispenser 310, on the downward stroke of the piston 356, and upon reaching the compression zone 436 of the slide 360, the relative hardness and geometry of the illustrated piston causes the piston to force the compression zone 436 of the slide outwardly and thereby form a fluid-tight seal between the piston and slide. As illustrated in FIG. 30, the tip of the guide wall 394 defines a chamfer for facilitating sliding movement of the piston within the slide.

Forming the integral nozzle and slide of a relatively soft and/or flexible material allows the compression zone 436 of the slide to flex outwardly in order to remove the part from a core pin upon molding the part, and thus enables the nozzle and slide to be integrally molded as a single part. Preferably, compressed air is injected between the core pin and interior surface 392 of the slide to facilitate removal of the part from the core pin (not shown).

As shown in FIGS. 19 and 20, when the flexible bladder 354 is at or near its fully-expanded condition, an annular gap "C" is formed between the bladder and vial. As can be seen, the width of the gap C gradually increases in the axial direction moving from the rear end cap 514 toward the closed end 476 of the bladder. As can be seen, the gap C starts about half-way down the axial extent of the bladder and reaches its maximum width at the curved portion of the bladder between the side wall and end wall 476. The gap C may be created by forming the approximately cylindrical side wall of the flexible bladder 354 with a sufficient draft to form the gap upon insertion of the bladder into the rigid vial. The purpose of the gradually-increasing gap C is to force all fluid within the main fluid chamber 355 in the direction toward the pump 350 and prevent the formation of any pockets of fluid within the main fluid chamber that cannot be dispensed therefrom.

As shown typically in FIGS. 19 and 20, other than the slight differences necessary to create the gap C, the flexible bladder 354 defines approximately the same morphology as the interior surfaces of the rigid vial 352, thus enabling intimate and conforming engagement of the bladder with the rigid vial upon full expansion of the bladder. In addition, the flexible bladder 354 preferably defines in its fully expanded condition an outer diameter (or width) at least equal to or greater than the inner diameter (or width) of the chamber 355 of the rigid vial. These features, in combination with the resilient nature of the flexible bladder, prevent the ingress of gases or vapors into the main fluid chamber 355, and ensure usage of substantially all fluid contained within the chamber.

Figure 32:
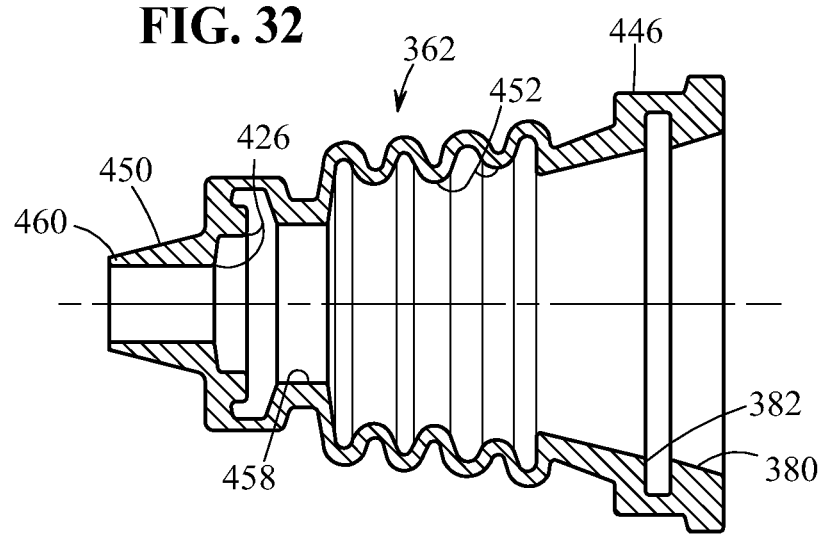
FIG. 32 is a cross-sectional view of the flexible nozzle cover and bellows of the dispenser of FIG. 17.

As shown in FIG. 32, the flexible cover 362 defines an annular mounting flange 380 on one end thereof which is received within a corresponding annular groove 374 formed on the integral piston and rigid vial (FIGS. 30 and 31) to fixedly secure the flexible cover thereto. In addition, the integral piston and rigid vial defines an annular flange 381 adjacent to the annular groove 374 which is received within a corresponding annular groove 382 of the flexible cover (FIG. 32) to further secure the cover thereto.

Figure 33:
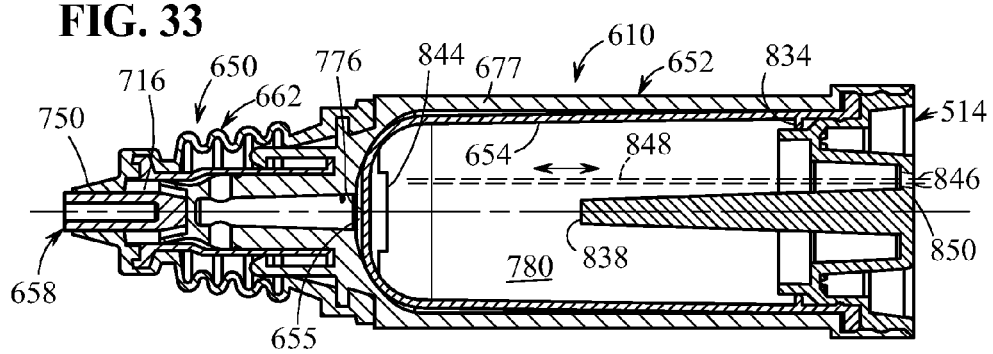
FIG. 33 is a cross-sectional view of another embodiment of the dispenser of the present invention including a resealable portion on the flexible bladder for inserting a needle or like injection member therethrough to fill the dispenser with a medicament or other substance, and allowing the needle holes to be sealed by application of thermal energy thereto.

Turning to FIG. 33, another embodiment of the dispenser of the present invention is indicated generally by the reference numeral 610. The dispenser 610 is substantially the same as the dispenser 310 described above, and therefore like reference numerals preceded by the numeral "6" instead of the numeral "3", the numeral "7" instead of the numeral "4", or the numeral "8" instead of the numeral "5", respectively, are used to indicate like elements. The primary difference of the dispenser 610 in comparison to the dispenser 310 is that the dispenser 610 includes a resealable bladder to allow the bladder to be filled in a sterile filling machine of the type disclosed in co-pending U.S. Pat. No. 6,604,561, granted Aug. 12, 2003, which is assigned to the same Assignee as the present invention, and is hereby expressly incorporated by reference as part of the present disclosure.

As shown in FIG. 33, the flexible bladder 654 includes on its closed end 776 a resealable portion 844 overlying the closed end 776. In the illustrated embodiment, the flexible bladder 354 is formed of a first material compatible with the predetermined medicament or other substance to be contained within the main fluid chamber 655, and defines on its external side a medicament-exposed surface intended to be exposed or otherwise placed in contact with the predetermined medicament or other substance contained within the main fluid chamber. The resealable portion 844 is penetrable by a needle or like filling member for introducing the predetermined medicament or other substance through the flexible bladder and into the main fluid chamber. The penetrable region of the flexible bladder is formed of a vulcanized rubber, and therefore is substantially infusible in response to the application of thermal energy thereto. The penetrable region of the resealable portion 844, on the other hand, is fusible in response to the application of thermal energy thereto, thus allowing the penetrable region of the resealable portion to be hermetically sealed upon removing the needle or like filling member therefrom. In the illustrated embodiment, the resealable portion 844 is insert molded onto the rubber bladder during which the thermoplastic resealable layer bonds itself to the underlying rubber layer. If necessary, a mechanical fastener of a type known to those skilled in the pertinent art may be used to facilitate attachment of the resealable portion to the end wall of the flexible bladder.

The resealable member 844 is preferably made of a resilient polymeric material, such as a blend of the polymeric material sold by GLS under the registered trademark KRATON® and a low-density polyethylene, such as the polyethylene sold by Dow Chemical Co. under the trademarks ENGAGE™ or EXACT™. An important feature of the resealable member 844 is that it be resealable to form a gas-tight seal after inserting a needle, syringe or like injection member through the resealable member. Preferably, the resealable member can be sealed by heating the area punctured by the needle in a manner known to those skilled in the pertinent art and described in the above-mentioned co-pending patent application. One advantage of the blended polymer described above is that it is known to minimize the degree to which the medicament or other substance can be absorbed into the polymer in comparison to KRATON® itself.

As shown in FIG. 33, the rear plug 514 defines a filling aperture 846 formed therethrough and overlying the resealable member 844. As shown in broken lines in FIG. 33, a double lumen needle or like injection member 848 may be reciprocally moved through the filling aperture 846 to, in turn, pierce both the resealable member 844 and underlying closed end 776 of the flexible bladder. The injection member 848 is coupled in fluid communication with a source (not shown) of medicament or other substance to be contained within the main fluid chamber 655 and is actuated to fill the chamber with the medicament or other substance. Upon filling the chamber, the flexible bladder 654 is collapsed into its predetermined collapsed condition, as shown above, and the needle is withdrawn. If necessary, a vacuum may be drawn on the interior chamber 780 of the flexible bladder during filling to facilitate collapse of the bladder. Upon withdrawing the needle, a laser or other energy source (not shown) transmits a beam of laser radiation onto the penetrated region of the resealable member to seal the needle hole in the manner described in the above-mentioned co-pending patent application and thereby maintain the medicament or other substance contained therein in a sterile, hermetically sealed condition. The filling aperture 846 may be sealed with a cap 850 (shown in broken lines) to maintain the interior chamber 780 of the flexible bladder in a sealed condition.

The laser or other energy source includes a laser or other suitable radiation source optically coupled to a scanning mirror. The laser includes a commercially available CO2 or YAG laser. The CO2 laser operates at a wavelength of approximately 10.6 μm. At this wavelength, absorption of the laser energy is governed by the electrical conductivity of the material. Therefore, an insulating material, such as the elastomeric material of the resealable member 844, absorbs and converts most of the incident energy into thermal energy to cauterize the receiving surface. The YAG laser operates at wavelength of approximately 1.06 μm. At this frequency, absorption is governed by the lattice atoms. Thus, a clear or transparent polymer with little ionization would be permeable to the laser beam. Accordingly, when employing a YAG laser, it is desirable to add a colorant to the elastomeric material of the resealable member in a manner known to those of ordinary skill in the pertinent art in order to enhance its absorption of the laser energy. A significant advantage of the YAG laser is that the superficial layer of the penetrable region of the resealable member, and any germs, bacteria or other contaminants thereon, are transformed into plasma to rapidly and thoroughly sterilize the effected surface. If necessary, a UV-filtration coating may be applied to the surfaces of the enclosure for the apparatus of the invention to prevent the operators from receiving any unnecessary UV exposure.

The present inventor has demonstrated that beam energies in the range of approximately 15 to 30 W are sufficient to effectively cauterize the surface of the elastomeric resealable member. In addition, bio-burden testing has demonstrated that laser energies of approximately 20 W or greater may achieve a 6.0 log reduction. At these energies, the apparatus of the present invention may effectively sterilize the surface within a cycle time of approximately 0.5 seconds. Accordingly, a significant advantage of the laser cauterization apparatus and method of the present invention is that they may involve significantly shorter cycle times than various direct heat methods. Yet another advantage of the laser cauterization of the present invention, is that it involves both a non-contact method and apparatus, and therefore there is no need to be concerned with the cleaning of a contact head or like heating surface.

After filling the dispenser with the medicament or other formulation and withdrawing the needle 848 from the resealable member 844, the penetrated region of the resealable member defines a needle hole along the path of the withdrawn needle. Upon withdrawing the needle 848, the vulcanized rubber base of the bladder is sufficiently resilient to close upon itself in the penetrated region and thereby maintain the dispenser in a sealed condition. However, vapors, gases and/or liquid may be allowed over time to pass through the needle hole, and therefore each dispenser is passed through a sealing station to heat seal the resealable portion promptly after withdrawing the needle therefrom. As indicated above, the laser source and scanning mirror are employed to heat seal the penetrated region of the resealable member. Accordingly, the same type of laser source and scanning mirror as described above may be employed in the heat sealing station to perform this function, or alternatively, a different type of laser system may be employed. In a currently preferred embodiment of the present invention, a CO2 laser of approximately 50 W is employed to seal a region approximately 0.10 inch in diameter in the resealable member.

One advantage of the illustrated dispenser is that the underlying rubber base of the resealable member thermally insulates the heated region from the medicament in the dispenser to thereby maintain the medicament in the dispenser within an appropriate temperature range throughout the cauterization and heat sealing processes and thereby avoid any thermal damage to the medicament.

As may be recognized by those skilled in the pertinent art based on the teachings herein, numerous changes and modifications may be made to the above-described and other embodiments of the present invention, without departing from its scope as defined in the appended claims. Accordingly, this detailed description of preferred embodiments is to be taken in an illustrative, as opposed to a limiting sense.

What is claimed is:

1. A device for aseptically receiving and dispensing substance comprising:
  a rigid housing having a flexible bladder defining a variable-volume storage chamber therein for receiving substance into the chamber, said storage chamber having a sealed inlet at one end thereof defined by a resealable portion, and an outlet for dispensing said substance out of the chamber;
  wherein the resealable portion is penetrable by an injection or filling member for introducing substance through the resealable portion and into the chamber, and is resealable to hermetically seal a penetrated region of the resealable portion after withdrawing the injection or filling member therefrom; and
  a pump coupled in fluid communication with the variable-volume storage chamber for pumping said substance from the chamber through the outlet.

2. A device as defined in claim 1, wherein the resealable portion comprises a resilient polymeric material.

3. A device as defined in claim 1, wherein substance within the chamber is sealed with respect to ambient atmosphere during dispensing of said substance through the outlet.

4. A device as defined in claim 1, further comprising an injection or filling member, coupled in fluid communication with a source of substance, configured to penetrate the resealable portion, and, in turn, to introduce said substance through the resealable portion and into the chamber.

5. A device as defined in claim 4, wherein the injection or filling member comprises a needle.

6. A device as defined in claim 1, wherein the resealable portion is resealable by application of radiation or energy thereto.

7. A device as defined in claim 6, wherein the radiation or energy comprises laser radiation.

8. A method of aseptically receiving into and dispensing substance from a device, the method comprising:
  penetrating with an injection or filling member a device comprising a rigid housing including a flexible bladder defining a variable-volume storage chamber therein for receiving substance into the chamber, said storage chamber having a sealed inlet at one end thereof defined by a resealable portion, and an outlet for dispensing said substance out of the chamber, wherein the resealable portion is penetrable by a injection or filling member for introducing substance therethrough and into the chamber, and is resealable to hermetically seal a penetrated region of the resealable portion after withdrawing the injection or filling member therefrom, and a pump coupled in fluid communication with the variable-volume storage chamber for pumping said substance from the chamber through the outlet;
  introducing substance from a source of said substance through the injection or filling member and into the chamber of the device; and
  dispensing said substance from the chamber through the outlet thereof.

9. A method as defined in claim 8, wherein the resealable portion comprises a resilient polymeric material.

10. A method as defined in claim 8, further comprising the step of maintaining substance within the chamber sealed with respect to ambient atmosphere during said dispensing step.

11. A method as defined in claim 8, wherein the injection or filling member comprises a needle.

12. A method as defined in claim 8, further comprising the step of withdrawing the injection or filling member from the resealable portion after said introducing step.

13. A method as defined in claim 12, further comprising, after said withdrawing step, the step of resealing the resealable portion, and, in turn, hermetically sealing a penetrated region thereof.

14. A device as defined in claim 13, wherein the resealable portion is resealable by application of radiation or energy thereto.

15. A device as defined in claim 14, wherein the radiation or energy comprises laser radiation.

16. A device for storing and dispensing a sterile fluid, comprising:
  a rigid outer body;
  a flexible inner bladder received within the outer body and defining a variable-volume storage chamber; and
  a one-way valve including a valve seat and an elastic valve member forming an interface with the valve seat and defining an interference fit therewith, the interface defining a normally closed valve opening, and an inlet to the interface defining a fluid flow path in fluid communication with the variable-volume storage chamber; and
  a pump coupled in fluid communication with the variable-volume storage chamber for pumping said sterile fluid from the chamber through the one-way valve,
  wherein the valve member is movable between a normally closed position, and an open position with at least a segment of the elastic valve member spaced away from its position in the closed position to connect the valve opening in fluid communication with a sterile fluid from the variable-volume storage chamber and thereby allow the passage of the sterile fluid through the valve opening,
  wherein the valve member is configured so that substantially throughout any period of dispensing fluid through the valve opening, a segment of the valve member engages the valve seat to maintain a hermetic seal between the inlet and ambient atmosphere, the variable-volume storage chamber is filled with the sterile fluid, the sterile fluid is hermetically sealed in the variable-volume storage chamber, and the flexible bladder and one-way valve maintain the sterile fluid within the variable-volume storage chamber sterile and hermetically sealed with respect to ambient atmosphere throughout dispensing a plurality of different portions of the sterile fluid from the storage chamber through the one-way valve.

17. A device as defined in claim 16, wherein the pump is configured for pumping a plurality of different portions of the sterile fluid from the variable-volume storage chamber through the one-way valve.

18. A device as defined in claim 16, further comprising, a sealed inlet at one end of the storage chamber defined by a resealable portion, and an outlet in fluid communication with the one-way valve for dispensing said substance out of the chamber, wherein the resealable portion is penetrable by an injection or filling member for introducing substance through the resealable portion and into the chamber, and is resealable to hermetically seal a penetrated region of the resealable portion after withdrawing the injection or filling member therefrom.

* * * * *